(12) United States Patent
Seo

(10) Patent No.: US 12,340,458 B2
(45) Date of Patent: Jun. 24, 2025

(54) IMAGE PROCESSING DEVICE, IMAGE PROCESSING METHOD, AND STORAGE MEDIUM FOR CONTROLLING THE DISPLAY OF THE SHAPE OF THE SURFACE REPRESENTED BY SURFACE DATA

(71) Applicant: Hirofumi Seo, Tokyo (JP)

(72) Inventor: Hirofumi Seo, Tokyo (JP)

( * ) Notice: Subject to any disclaimer, the term of this patent is extended or adjusted under 35 U.S.C. 154(b) by 140 days.

(21) Appl. No.: 18/014,122

(22) PCT Filed: Jul. 5, 2021

(86) PCT No.: PCT/JP2021/025373
§ 371 (c)(1),
(2) Date: Dec. 30, 2022

(87) PCT Pub. No.: WO2022/004898
PCT Pub. Date: Jan. 6, 2022

(65) Prior Publication Data
US 2023/0260198 A1     Aug. 17, 2023

(30) Foreign Application Priority Data
Jul. 3, 2020   (JP) ................................ 2020-116005

(51) Int. Cl.
G06T 15/08      (2011.01)
G06T 19/00      (2011.01)
A61B 6/03       (2006.01)

(52) U.S. Cl.
CPC .............. *G06T 15/08* (2013.01); *G06T 19/00* (2013.01); *A61B 6/032* (2013.01);
(Continued)

(58) Field of Classification Search
CPC . G06T 19/00; G06T 2200/24; G06T 2210/21; G06T 15/08; G06T 2210/41;
(Continued)

(56) References Cited

U.S. PATENT DOCUMENTS

2004/0051710 A1   3/2004   Hara
2005/0022158 A1   1/2005   Launay et al.
(Continued)

FOREIGN PATENT DOCUMENTS

JP   2004230166 A   8/2004
JP   2008018016 A   1/2008
(Continued)

OTHER PUBLICATIONS

Nain, Delphine. An interactive virtual endoscopy tool with automotive path generation. Diss. Massachusetts Institute of Technology (Year: 2022).*
(Continued)

*Primary Examiner* — Maurice L. McDowell, Jr.
(74) *Attorney, Agent, or Firm* — Holtz, Holtz & Volek PC

(57) ABSTRACT

An image processing device includes a UI controller and a rendering processor. The rendering processor obtains, from volume data constituted by multiple points, each point having a value, surface data representing the shape of a surface. The shape of the surface is defined by magnitude of each of the values. The UI controller sets a threshold for the values to determine whether to display the surface data. The rendering processor determines an intersecting point at which a straight line passing through a position set as a viewpoint and a point specified by a user intersects with the shape of the surface which is to be displayed in accordance with the threshold. Based on a plane passing through the intersecting point, the rendering processor controls the displaying of the shape of the surface represented by the surface data.

12 Claims, 22 Drawing Sheets

(52) U.S. Cl.
CPC ...... *G06T 2200/24* (2013.01); *G06T 2210/21* (2013.01); *G06T 2210/41* (2013.01)

(58) Field of Classification Search
CPC . G06T 2219/028; A61B 6/032; A61B 6/5205; A61B 6/466; A61B 6/468; A61B 6/469
See application file for complete search history.

(56) References Cited

U.S. PATENT DOCUMENTS

| | | | |
|---|---|---|---|
| 2011/0118596 A1* | 5/2011 | Vining | G06T 7/155 600/425 |
| 2012/0113111 A1* | 5/2012 | Shiki | A61B 8/463 345/419 |
| 2014/0081141 A1 | 3/2014 | Nishihara et al. | |
| 2016/0306936 A1 | 10/2016 | Mizobe | |
| 2019/0347839 A1* | 11/2019 | Sakuragi | G06T 19/20 |
| 2020/0027546 A1 | 1/2020 | Nasu | |
| 2020/0151874 A1 | 5/2020 | Peterson et al. | |

FOREIGN PATENT DOCUMENTS

| | | |
|---|---|---|
| JP | 2009136665 A | 6/2009 |
| JP | 2011010715 A | 1/2011 |
| JP | 2012239820 A | 12/2012 |
| JP | 2013013650 A | 1/2013 |
| JP | 2013236750 A | 11/2013 |
| JP | 2016202904 A | 12/2016 |
| JP | 2020014551 A | 1/2020 |
| WO | 2018159709 A1 | 9/2018 |

OTHER PUBLICATIONS

International Search Report (ISR) (and English translation thereof) dated Sep. 21, 2021, issued in International Application No. PCT/JP2021/025373.

Written Opinion dated Sep. 21, 2021, issued in International Application No. PCT/JP2021/025373.

Haraguchi, et al., "Improvement of representation for three-dimensional reconstruction and visualization of serial histological specimens", The Institute of Electronics Information and Communication Engineers (IEICE) Technical Report, pp. 125-128, Mar. 2015.

Nakashima, et al., "Interactive Deformation of Structurally Complex Heart Models Constructed from Medical Images", Preprints of Visual Computing / Graphics and CAD Joint Symposium 2016.

Extended European Search Report (EESR) dated Mar. 15, 2024, issued in counterpart European Application No. 21834498.4.

Partial Supplementary European Search Report dated Dec. 11, 2023, issued in counterpart European Application No. 21834498.4.

Lorensen, et al., "Marching Cubes a High Resolution 3D Surface Construction Algorithm", Computer Graphics Proceedings; Annual Conference Series; SIGGRAPH; Aug. 1, 1987; pp. 163-169.

Marovic, et al., "Visualization of 3D fields and medical data and using VRML", Future Generation Computer Systems, Elsevier Science Publishers; Amsterdam, NL, vol. 14, No. 1-2, Jun. 1, 1998, pp. 33-49.

* cited by examiner

FIG. 2

| EDGE NUMBER | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|---|---|---|---|---|
| FLAG | 0 | 0 | 1 | 1 | 0 | 0 | 0 | 0 | 1 | 0 | 0 | 0 | 0 | 1 | 0 | 1 | 1 | 0 | 1 | 1 | 0 | 0 | 0 | 1 | 0 | 0 | 0 | 0 | 1 | 0 | 0 | 0 |
| HASH VALUE | 0 | 0 | 0 | 1 | 2 | 2 | 2 | 2 | 2 | 3 | 3 | 3 | 3 | 3 | 4 | 4 | 5 | 6 | 6 | 7 | 8 | 8 | 8 | 8 | 9 | 9 | 9 | 9 | 9 | 10 | 10 | 10 |

FIG. 4
CASE (A) IN WHICH ONE THRESHOLD IS SET
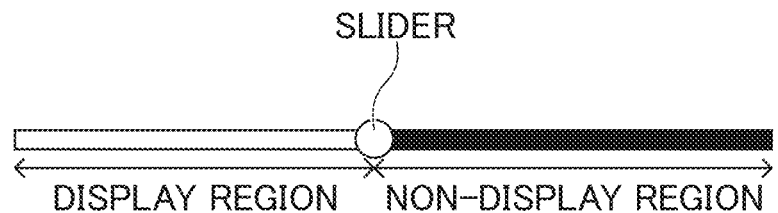
CASE (B) IN WHICH TWO THRESHOLDS ARE SET
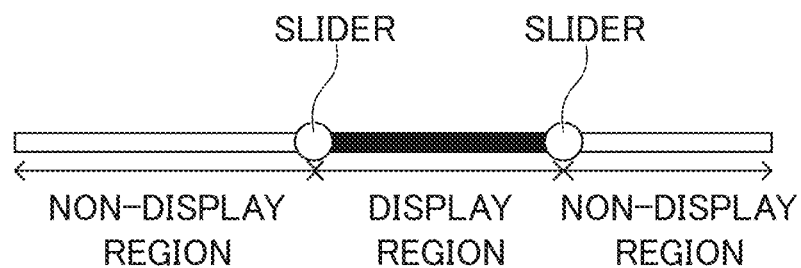
CASE (C) IN WHICH AN AUXILIARY SLIDER IS DISPLAYED
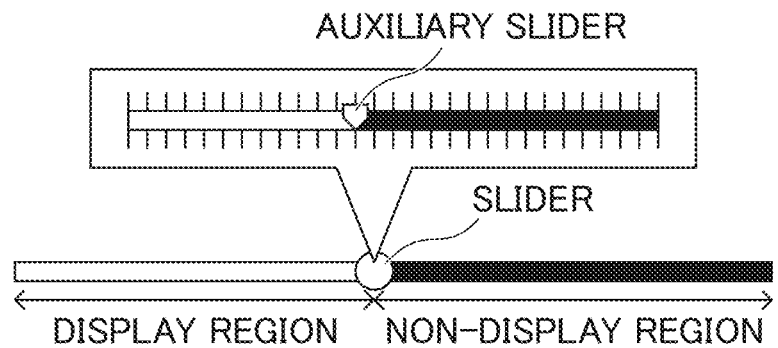

FIG. 9
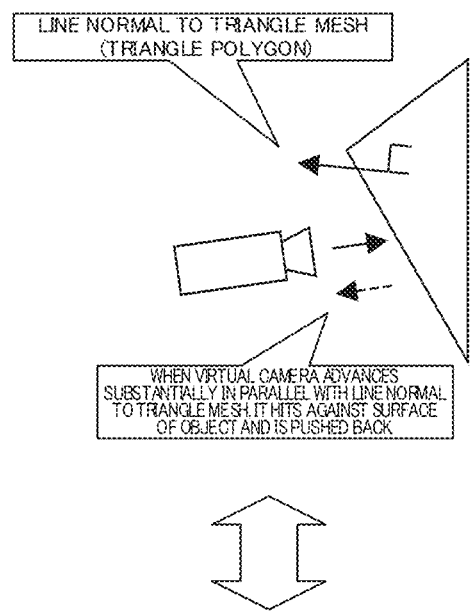
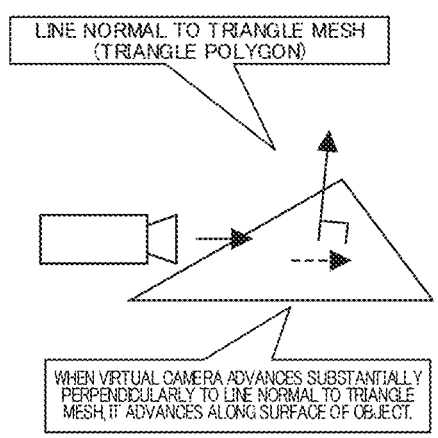

FIG. 18

| EDGE NUMBER | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|---|---|---|---|---|
| FIRST FLAG | 0 | 0 | 1 | 1 | 0 | 0 | 0 | 0 | 1 | 0 | 0 | 0 | 1 | 0 | 1 | 1 | 0 | 1 | 1 | 0 | 0 | 0 | 0 | 1 | 0 | 0 | 0 | 0 | 1 | 0 | 0 | 0 |
| SECOND FLAG | 0 | | 2 | | 0 | | 0 | | 1 | | 0 | | 1 | | 1 | | 1 | | 2 | | 0 | | 1 | | 0 | | 0 | | 1 | | 0 | |
| HASH VALUES | 0 | | 0 | | 2 | | 2 | | 2 | | 3 | | 3 | | 4 | | 5 | | 6 | | 8 | | 8 | | 9 | | 9 | | 9 | | 10 | |
| Pixel ID | 0 | | 1 | | 2 | | 3 | | 4 | | 5 | | 6 | | 7 | | 8 | | 9 | | 10 | | 11 | | 12 | | 13 | | 14 | | 15 | |

FIG. 20
ORIGINAL TECHNIQUE
SECOND MODIFIED EXAMPLE TECHNIQUE

FIG. 21
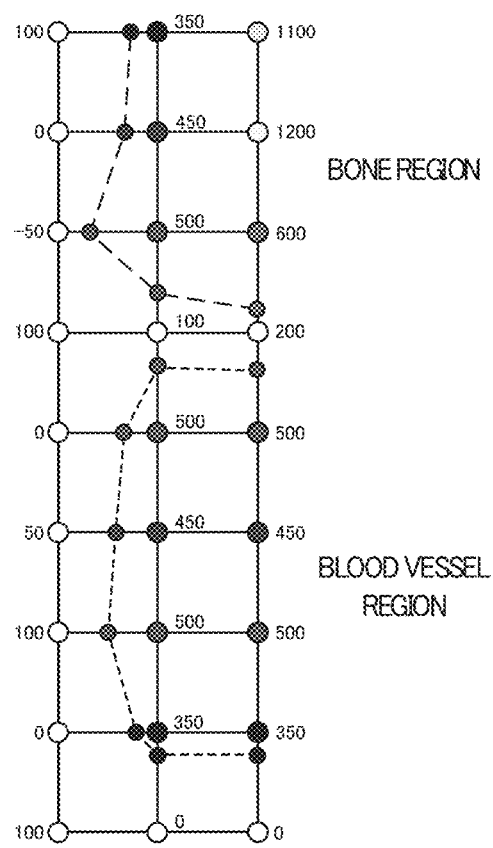
(a) COLORS OF SURFACES SUBJECTED TO LINEAR INTERPOLATION
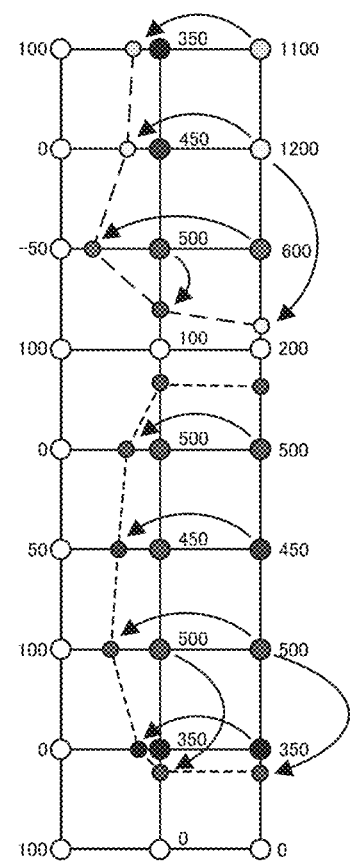
(b) COLOR CORRECTION METHOD FOR THE SURFACES OF OBJECTS IN THE THIRD MODIFIED EXAMPLE FIG. 22
ORIGINAL TECHNIQUE
THIRD MODIFIED EXAMPLE TECHNIQUE

FIG. 23
(a) PART OF THE COLOR CORRECTION METHOD FOR THE SURFACES OF OBJECTS IN THE THIRD MODIFIED EXAMPLE
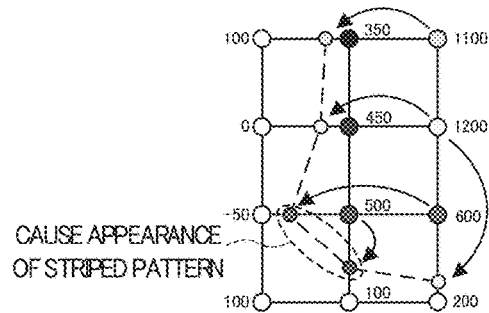
CAUSE APPEARANCE OF STRIPED PATTERN
(b) IN THE PROCESS OF EXECUTING THE COLOR CORRECTION METHOD FOR THE SURFACES OF OBJECTS IN THE FOURTH MODIFIED EXAMPLE
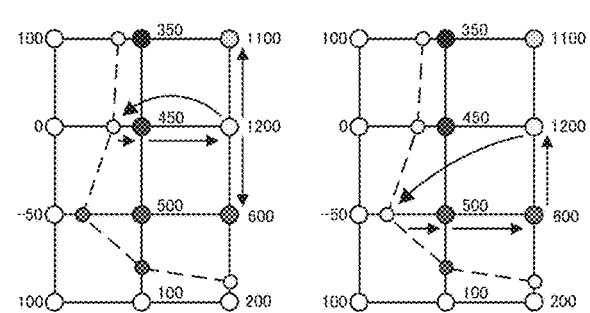
(c) PART OF THE COLOR CORRECTION METHOD FOR THE SURFACES OF OBJECTS IN THE FOURTH MODIFIED EXAMPLE
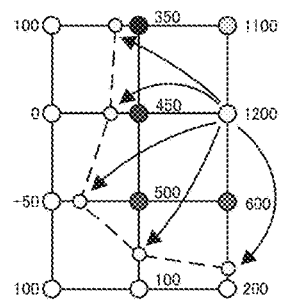

FIG. 24
ORIGINAL TECHNIQUE
FOURTH MODIFIED EXAMPLE TECHNIQUE

IMAGE PROCESSING DEVICE, IMAGE PROCESSING METHOD, AND STORAGE MEDIUM FOR CONTROLLING THE DISPLAY OF THE SHAPE OF THE SURFACE REPRESENTED BY SURFACE DATA

TECHNICAL FIELD

The present invention relates to an image processing device, an image processing method, and a storage medium.

BACKGROUND ART

Hitherto, various technologies have been proposed to display three-dimensional image data.

Typically, medical images obtained by CT (Computed Tomography) or MRI (Magnetic Resonance Imaging) are constituted by volume data including information of the length, width, and height. To display such volume data, surface rendering techniques are widely utilized.

A rendering technique for volume data is disclosed in PTL 1, for example.

CITATION LIST

Patent Literature

[PTL 1] Japanese Unexamined Patent Application Publication No. 2020-014551

SUMMARY OF INVENTION

Technical Problem

In the related art, however, when visualizing an object subjected to surface rendering, it is not always easy to display the object in various display modes so as to satisfy user's demands. For example, triangle meshes formed by performing surface rendering become independent of each other, depending on a technique used for surface rendering. In a state in which triangle meshes are independent of each other, it is not possible to move a triangle mesh of interest and its adjacent triangle mesh together. This makes it difficult to execute some processing, such as changing of the shape of an object subjected to surface rendering.

In this manner, in the related art, it is difficult to visualize a three-dimensional image appropriately.

Solution to Problem

An image processing device according to an aspect of the present invention comprising:
- a surface data obtaining means for obtaining, from volume data constituted by a plurality of points, each point having a value, surface data representing a shape of a surface, the shape of the surface being defined by magnitude of each of the values;
- a threshold setting means for setting a threshold for the values, the threshold being used to determine whether to display the surface data;
- an intersecting-point determining means for determining an intersecting point at which a straight line passing through a position set as a viewpoint and a point specified by a user intersects with the shape of the surface which is to be displayed in accordance with the threshold; and
- a display control means for controlling, based on a plane passing through the intersecting point, displaying of the shape or the surface represented by the surface data.

BRIEF DESCRIPTION OF DRAWINGS

FIG. 2 is a schematic diagram illustrating an example of the vertex-position determining table.

FIG. 4 shows schematic views illustrating specific modes of the threshold setter D3.

FIG. 9 shows schematic views illustrating examples of the display mode at the first person viewpoint.

FIG. 18 is a schematic diagram illustrating a modified example of the vertex-position determining table.

FIG. 20 shows schematic views illustrating an example of a comparison result obtained by displaying different objects together with one threshold according to the color correction method of this modified example.

FIG. 21 shows schematic diagrams illustrating a color correction method for the surfaces of objects of volume data whose boundary not clearly expressed between adjacent voxels.

FIG. 22 shows schematic views illustrating an example of a comparison result obtained by displaying different objects together with one threshold according to the color correction method of this modified example.

FIG. 23 shows schematic diagrams illustrating an example of a color correction method to select voxels around a vertex of a triangle mesh as voxels to be selected based on the coloring-reference-voxel selection condition.

FIG. 24 shows schematic views illustrating an example of a comparison result obtained by displaying different objects together with one threshold according to the color correction method of the present modified example.

DESCRIPTION OF EMBODIMENTS

Hereinafter, an embodiment of the invention will be described below with reference to the drawings.

First Embodiment

[Configuration]

Figure 1:
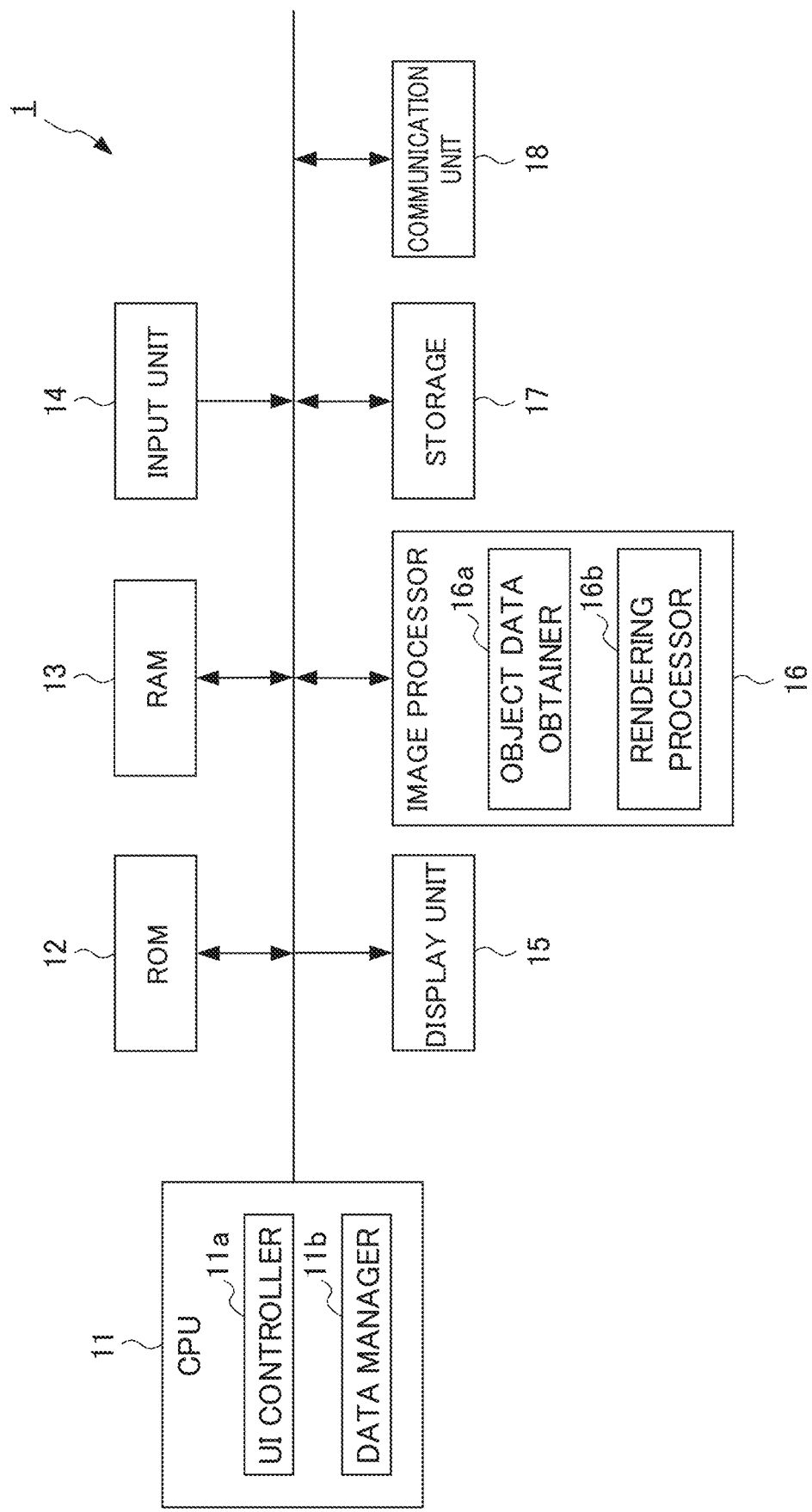
FIG. 1 is a block diagram illustrating the configuration of an image processing device 1 according to an embodiment of the invention.

FIG. 1 is a block diagram illustrating the configuration of an image processing device 1 according to an embodiment of the invention.

The image processing device 1 is constituted by an information processing device, such as a PC (Personal Computer) or a tablet terminal.

As shown in FIG. 1, the image processing device 1 includes a CPU (Central Processing Unit) 11, a ROM (Read Only Memory) 12, a RAM (Random Access Memory) 13, an input unit 14, a display unit 15, an image processor 16, a storage 17, and a communication unit 18.

The CPU 11 controls the entirety of the image processing device 1 by executing various programs stored in the storage 17. For example, the CPU 11 executes a program for executing visualizing processing of surface data (such as data of a tomographic image captured by CT or MRI) generated from volume data (hereinafter, such visualizing processing will be called "object display processing"). When executing object display processing, the CPU 11 allocates some tasks to the image processor 16, which will be discussed later, to implement efficient processing in the overall image processing device 1. For example, while the CPU 11 is capable of flexibly executing various types of processing, the image processor 16 is capable of executing similar arithmetic processing operations repeatedly at high speed. By considering these capabilities, the CPU 11 executes the entire processing in collaboration with the image processor 16 in accordance with the type of processing.

As a result of executing the program for object display processing, a user interface controller (UI controller) 11a and a data manager 11b are formed in the CPU 11 as the functional configuration.

The UI controller 11a controls the displaying of various input/output screens (hereinafter called "UI screen") used for the image processing device 1 to execute various processing operations, such as object display processing. For example, the UI controller 11a displays surface data generated from volume data in various display modes on the UI screen. In the present embodiment, the UI controller 11a displays an initial UI screen that displays surface data and displays multiple menus on the initial UI screen, so that it can receive an instruction to shift to a screen which displays surface data in a specific display mode. Examples of the UI screen displayed by the image processing device 1 will be discussed later.

In response to a user instruction, the data manager 11b stores image data of an object displayed on the UI screen in the storage 17 and obtains object data (volume data or surface data) from another device (system server in a hospital, for example).

In the ROM 12, various system programs for controlling the image processing device 1 are prestored.

The RAM 13 is constituted by a semiconductor memory, such as a DRAM (Dynamic Random Access Memory), and stores data generated as a result of the CPU 11 executing various processing operations.

The input unit 14 is constituted by an input device, such as a keyboard and a mouse or a touch sensor (touchscreen), and receives various types of information to be input into the image processing device 1 from a user.

The display unit 15 is constituted by a display device, such as a LCD (Liquid Crystal Display), and displays results of various processing operations executed by the image processing device 1.

The image processor 16 is constituted by hardware such as a graphic accelerator) including a GPU (Graphic Processing Unit), and executes processing for displaying images in the image processing device 1. The image processor 16 includes a local memory (not shown) for executing image processing. In the present embodiment, when the CPU 11 executes object display processing, the image processor 16 executes specific processing in response to an instruction from the CPU 11.

As a result of the CPU 11 executing the program for object display processing, an object data obtainer 16a and a rendering processor 16b are formed in the image processor 16 as the functional configuration.

The object data obtainer 16a reads object data stored in the storage 17 in response to an instruction from the CPU 11.

In response to an instruction from the CPU 11, the rendering processor 16b performs rendering processing to display object data read by the object data obtainer 16a on the UI screen, and displays a rendering processing result (that is, data which is rasterized to be displayed) on the display unit 15. In the present embodiment, object data obtained by the object data obtainer 16a is surface data generated from volume data, and triangle meshes forming surface data are connected with each other. However, if an instruction to perform rendering for converting volume data into surface data (surface rendering) is provided from the CPU 11, the rendering processor 16b executes rendering processing for converting volume data into surface data so as to generate surface data constituted by triangle meshes connected with each other. For example, in certain situations, such as those where surface data of an object is not yet generated from volume data and where, during object display processing, a new surface is generated as a result of an object being cut in a virtual manner, for example, the rendering processor 16b executes rendering processing for converting volume data into surface data.

In the present embodiment, when performing rendering for converting volume data into surface data, the rendering processor 16b executes processing at high speed while determining the relationships between the voxels representing the volume data and the vertices of triangle meshes forming surface data by using table format data indicating this relationship (hereinafter such table format data will be called "vertex-position determining table").

FIG. 2 is a schematic diagram illustrating an example of the vertex-position determining table.

As shown in FIG. 2, in the first row of the vertex-position determining table, the number for identifying the edge of a voxel representing volume data is stored.

In the second row of the vertex-position determining table, a flag indicating whether or not a vertex of a triangle mesh is present on an individual edge in the first row (if a vertex is present, the flag indicates "1", and if no vertex is present, the flag indicates "0") is stored. Whether a vertex of a triangle mesh is present on an edge can be determined based on whether the values of voxels located at both ends of the edge have a predetermined difference (which is a value greater than or equal to a threshold used for determining whether the edge between voxels is a surface).

In the third row of the vertex-positon determining table, the hash value determined based on the number for identifying the edge in the first row and the flag in the second row for this edge is stored. For the n-th (n is a natural number) edge, for example, the hash value in the third row is calculated by adding the hash value of the (n−1)-th edge and the flag of the (n−1)-th edge. The hash value of the 0-th edge is 0 in this example, but a desirable value may be set. In this manner, the hash values in the vertex-position determining table can be calculated by the above-described sequential addition processing. Hence, as a result of the image processor 16 executing this processing, high-sped processing can be implemented.

By referring to the third row in the vertex-position determining table, the edge on which the m-th (m is an integer of 0 or greater) vertex (vertex of a triangle mesh) is present can easily be identified. This can further increase the speed of executing processing for generating surface data from volume data.

Referring back to FIG. 1, the storage 17 is constituted by a non-volatile storage device, such as a hard disk or a flash memory, and stores a program for object display processing, for example. The storage 17 also stores object data (volume data or surface data) and results of various processing operations executed by the image processing device 1 (such as image data represented in a specific display mode generated by the image processor 16).

The communication unit 18 includes a communication interface that performs signal processing based on a predetermined communication standard, such as a wired or wireless LAN (Local Area Network) and USB (Universal Seral Bus). The communication unit 18 controls communication performed by the image processing device 1 with another device.

[Specific Examples of UI Screen]

Specific examples of the UI screen displayed by the image processing device 1 will be discussed below.

The UI screen has a function of receiving various instructions (such as that to shift to a specific display mode and that to change a threshold used for displaying an object) from a user, as well as displaying object data subjected to rendering processing performed by the image processor 16.

[Initial UI Screen]

The initial UI screen is a home screen to be displayed when object display processing is executed.

Figure 3:
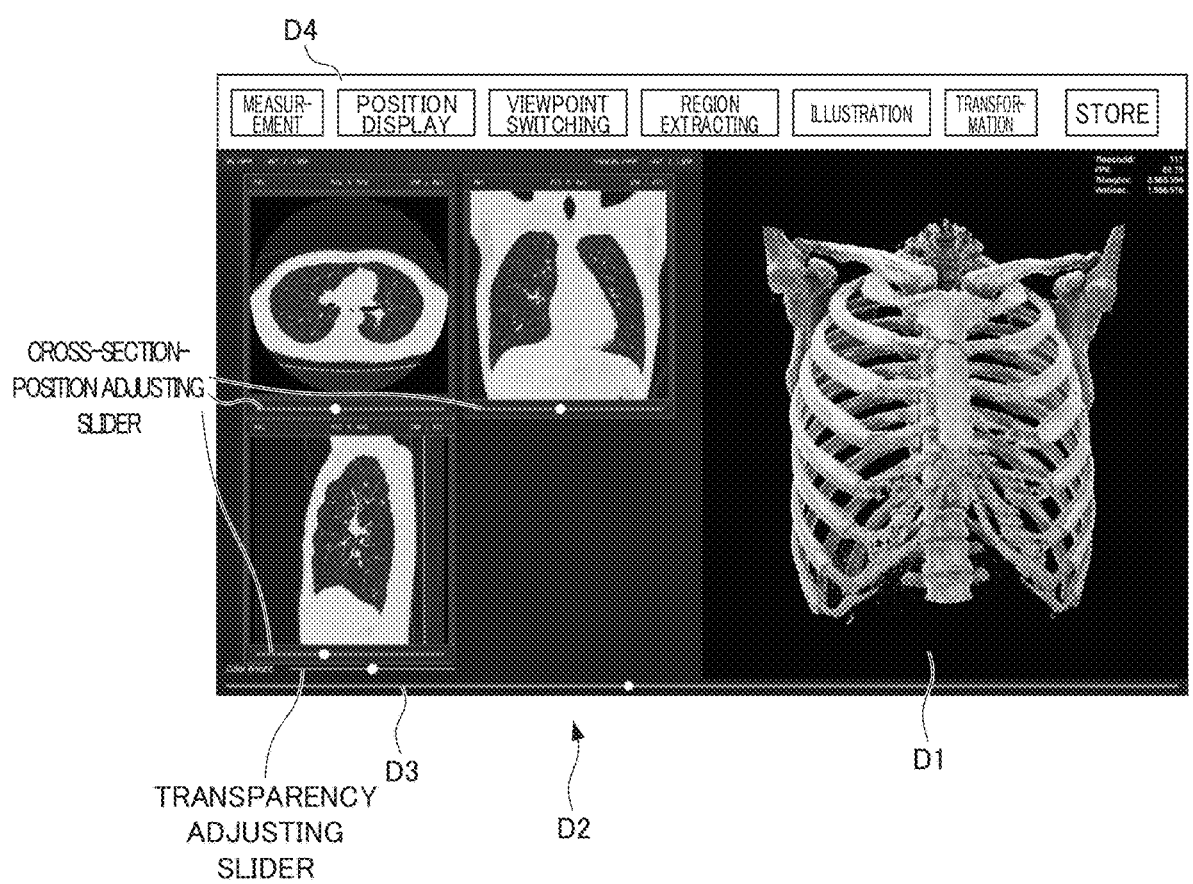
FIG. 3 is a schematic view illustrating an example of the initial UI screen.

FIG. 3 is a schematic view illustrating an example of the initial UI screen.

As shown in FIG. 3, the initial UI screen includes screens on which a subject object is displayed (a three-dimensional image display D1 and a sectional image display D2), a threshold setter D3 for setting a threshold for displaying an object as a surface, and an instructor D4 for calling a function, such as that for displaying an object in a specific display mode. In FIG. 3, a "cross-section-position adjusting slider" for adjusting the position of a sectional image displayed in the sectional image display D2 and a "transparency adjusting slider" for adjusting the level of transparency of the image filling are also displayed.

In the three-dimensional image display D1, a three-dimensional image of an object represented as a surface based on the threshold set by the threshold setter D3 is displayed. In accordance with the purpose of use of a user, for example, a sectional image may be displayed in the three-dimensional image display D1, or the entire screen may be used as the three-dimensional image display D1 without displaying other screens such as the sectional image display D2.

In the sectional image display D2, not only a three-view drawing at a desired location of volume data, but also a sectional image of an object which is cut in cross section at a point specified on the three-dimensional image display D1 can be displayed. In a sectional image displayed in the sectional image display D2, too, a surface based on the threshold set by the threshold setter D3 is displayed.

When displaying an object as a three-dimensional image, the rendering processor 16b determines a point at which a half-line passing through a camera position (viewpoint) and a mouse cursor position intersects with a triangle mesh forming surface data, and sets this intersecting point to be a reference point for displaying a three-dimensional image or a sectional image. For example, the rendering processor 16b may use this intersecting point as a center point when rotating a displayed object.

At this time, if the threshold is adjusted with the threshold setter D3, the state of the displayed object (more specifically, the state of the surface of the object) is changed. In this case, a portion of the object which is not displayed (body surface, for example) is treated as if it were not present, and the intersecting point with the currently displayed object is calculated as the "intersecting point".

When the state of the displayed object is changed as a result of the threshold being adjusted with the threshold setter D3, the positions of the vertices of triangle meshes can be determined by using the above-described vertex-position determining table. Determining the positions of the vertices in this manner can change the state of the object quickly.

By using such a display mode, when a user comes across a portion of the object that the user wishes to see by changing the threshold, the object can be rotated about a point thereon (or a cross section can be displayed at this point, for example), thereby further enhancing the operability for viewing a three-dimensional object.

When a user specifies a plane, which is a cross section, in the three-dimensional image display D1, the rendering processor 16b can display surface data (triangle meshes) located only on one side with respect to the cross section (the side above the cross section, for example) and not display surface data on the other side (the side below the cross section, for example).

The threshold setter D3 forms a user interface which sets a threshold for displaying an object as a surface. The threshold setter D3 can consecutively set thresholds by using a slider, for example. In the present embodiment, the threshold setter D3 may set multiple thresholds for displaying an object.

FIG. 4 shows schematic views illustrating specific modes of the threshold setter D3.

For existing CT images, for example, the following display mode is employed. One threshold is set, and if a corresponding value of an object is smaller than the threshold, the object is displayed, and if the corresponding value is greater than or equal to the threshold, the object is not displayed. The threshold setter D3 may use this display mode, as in "case (A) in which one threshold is set" shown in FIG. 4.

In contrast, as in "case (B) in which two thresholds are set" in FIG. 4, the threshold setter D3 may set plural (two, for example) thresholds and only display voxels whose values are in a range between the plural thresholds.

In this display mode, the effective region of the thresholds is limited to the range between specific values. More thresholds may be set, in which case, two or more effective regions can be set.

When setting a threshold by using a slider, to set a threshold in a more detailed range than the sliding range of the slider, an auxiliary slider which displays a scale in a limited range may be displayed, such as in "case (C) in which an auxiliary slider is displayed" in FIG. 4.

Referring back to FIG. 3, in the instructor D4, icons for calling various menus regarding object displaying or processing that can be executed by the image processing device 1 are displayed.

[Physical-Quantity Measuring Screen]

A physical-quantity measuring screen is a screen to be displayed when a "measure" menu in the instructor D4 is called on the initial UI screen.

On the physical-quantity measuring screen, physical quantities, such as the distance and the volume, of a displayed object can be measured as a result of an operation performed on the UI screen.

Figure 5:
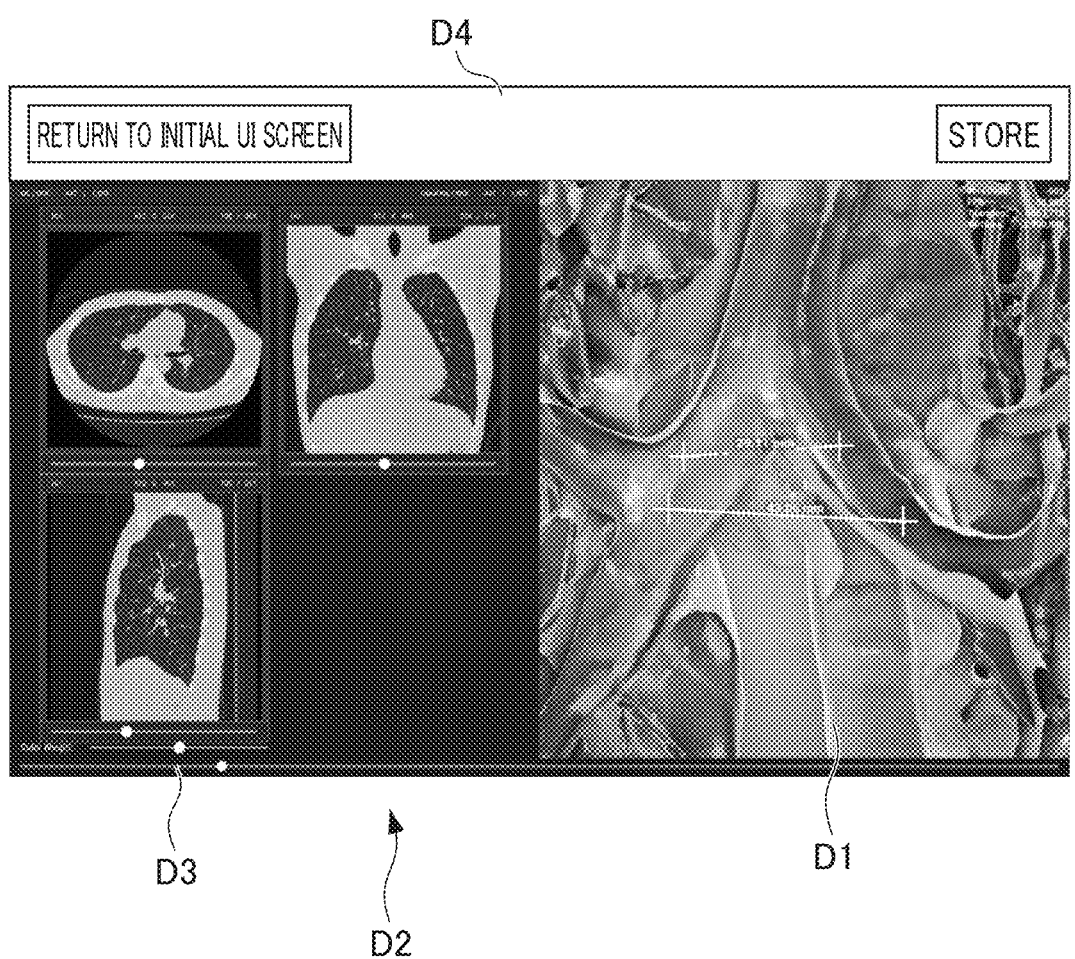
FIG. 5 is a schematic view illustrating an example of the physical-quantity measuring screen.

FIG. 5 is a schematic view illustrating an example of the physical-quantity measuring screen.

On the physical-quantity measuring screen, as well as on the initial UI screen, the three-dimensional image display D1, the sectional image display D2, and the threshold setter D3 are displayed. In the instructor D4, an icon for returning to the initial UI screen and an icon for storing results of measuring the physical quantities on the physical-quantity measuring screen are displayed.

On the physical-quantity measuring screen shown in FIG. 5, in response to specifying of a point, a line segment, a curve, or a range on a three-dimensional image or a sectional image, a physical quantity of the object is measured (calculated) and measurement results are displayed on the screen of the object. In the example in FIG. 5, the result of measuring the distance on a surface between two points (measurement result on the upper side of the three-dimensional image display D1) and the result of measuring the distance on a cross section between two points (measurement result on the lower side of the three-dimensional image display D1) are shown.

When measuring a physical quantity, an attribute of a measurement subject can be changed by performing a certain operation, such as specifying a point on the surface of an object with the left mouse button and specifying a point on a cross section of the object with the right mouse button.

As the physical quantities that can be measured, the distance on a cross section, the distance on a surface, and the area or the volume on a surface (for example, a region surrounded by a closed curved surface, such as a heart), for example, can be selected.

[Position Display Screen]

A position display screen is a screen to be displayed when a "position display" menu in the instructor D4 is called on the initial UI screen or a screen to be displayed when a specific key of the keyboard, for example, in the input unit 14 is being pressed.

On the position display screen, it is possible to display, at least on a sectional image, at which position of an object a specified voxel is located.

Figure 6:
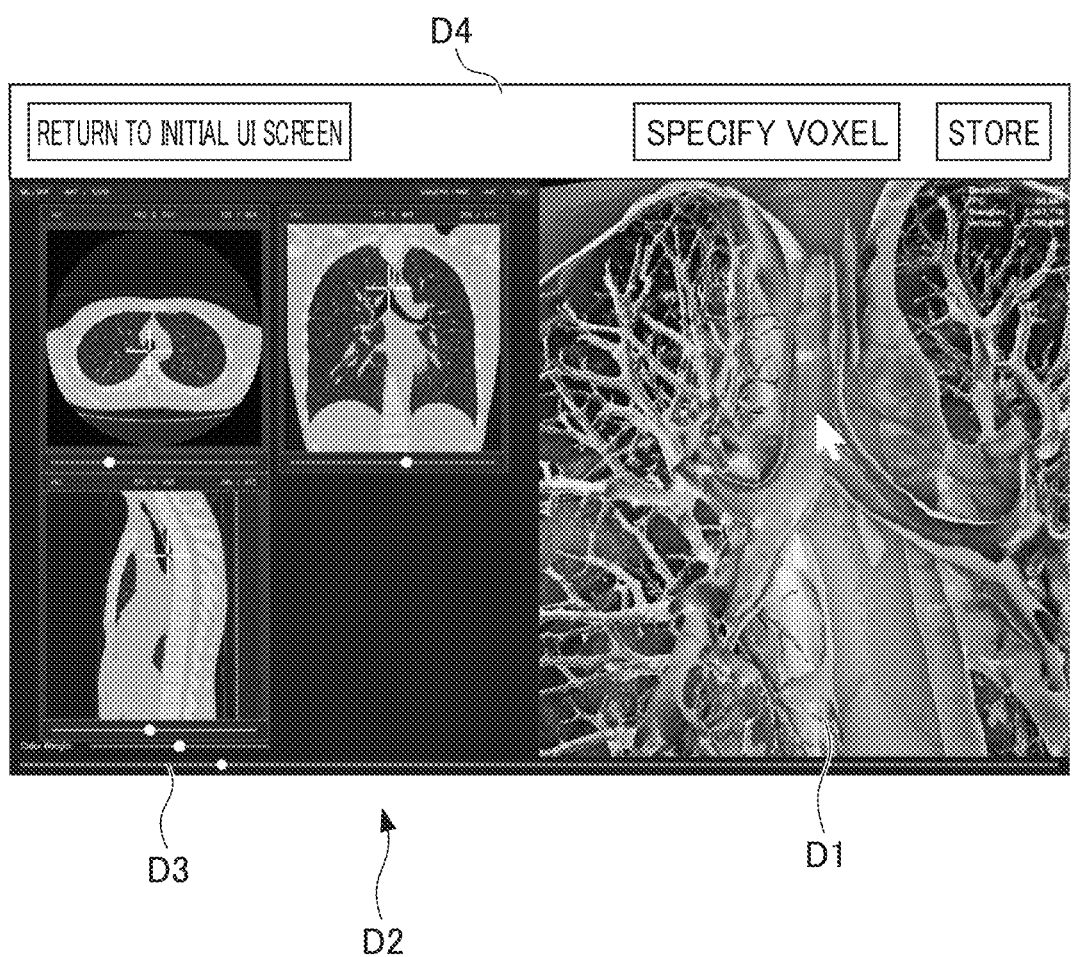
FIG. 6 is a schematic view illustrating an example of the position display screen.

FIG. 6 is a schematic view illustrating an example of the position display screen.

On the position display screen, as well as on the initial UI screen, the three-dimensional image display D1, the sectional image display D2, and the threshold setter D3 are displayed. In the instructor D4, icons, such as an icon for returning to the initial UI screen, an icon for specifying a voxel, and an icon for storing a display result of a voxel on the position display screen, are displayed.

When a user specifies a certain point on the surface of an object in the three-dimensional image display D1, the specified voxel may not be present in a cross section currently displayed in the sectional image display D2.

To deal with such a case, as shown in FIG. 6, on the position display screen, a sectional image to be displayed in the sectional image display D2 is shifted to the position of the specified voxel. In this manner, it is possible to show, at least on a sectional image, where the specified voxel is located.

When a user specifies a certain point on a sectional image in the sectional image display D2, a cross section other than the specified sectional image may not be displayed or a specified voxel may not be displayed in the three-dimensional image display D1. To deal with such a case, the sectional image to be displayed in the sectional image display D2 is shifted to the position of the specified voxel. In the three-dimensional image display D1, in certain situations, such as where the inside of an object or a voxel located at the back of the object is specified, the specified voxel may not be seen on a three-dimensional image represented by surface data. In this case, for example, a cross section in the three-dimensional image display D1 is shifted to a position at which the cross section passes through the specified voxel. This makes it possible to constantly check the position of a specified voxel in the three-dimensional image display D1.

With this configuration, when a user wishes to check a specific part of an object, he/she can easily identify the corresponding voxel to be checked.

[Viewpoint Switching Screen]

A viewpoint switching screen is a screen to be displayed when a "viewpoint switch" menu in the instructor D4 is called on the initial UI screen or a screen to be displayed when a specific key of the keyboard, for example, in the input unit 14 is being pressed.

In the viewpoint switching screen, the camera viewpoint can be determined by switching between a third person viewpoint (viewpoint seen from outside) and a first person viewpoint (subjective viewpoint, such as looking up and looking down).

Figure 7:
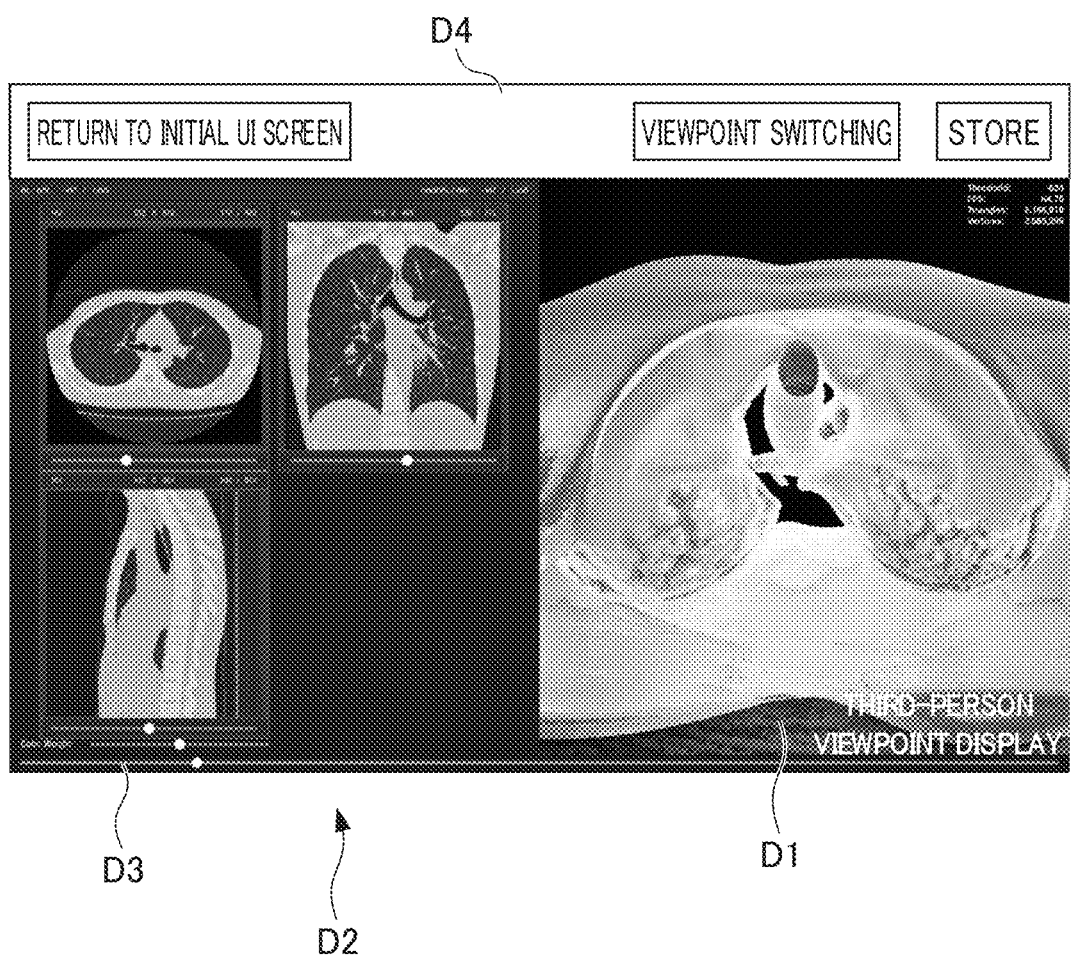
FIG. 7 is a schematic view illustrating an example (in the case of the third person viewpoint) of the viewpoint switching screen.
Figure 8:
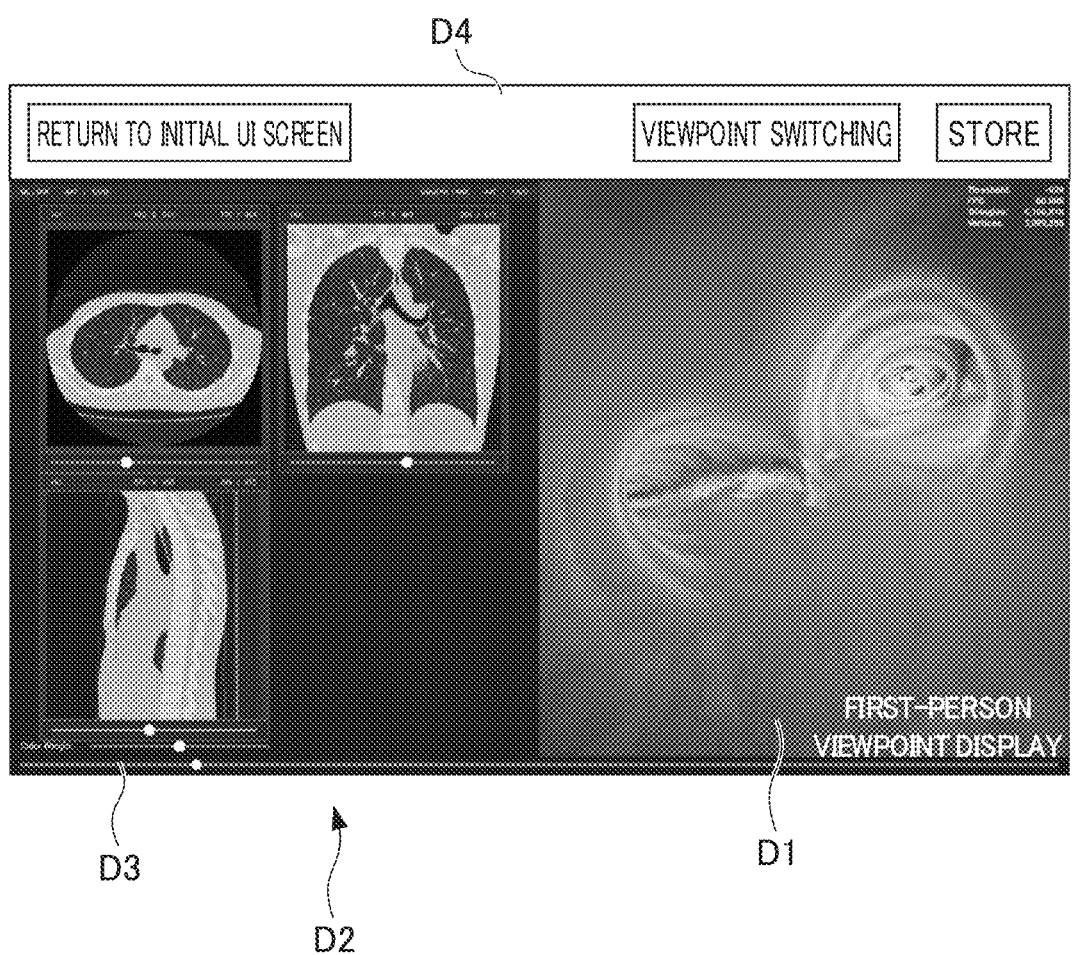
FIG. 8 is a schematic view illustrating an example (in the case of the first person viewpoint) of the viewpoint switching screen.

FIG. 7 is a schematic view illustrating an example (in the case of the third person viewpoint) of the viewpoint switching screen. FIG. 8 is a schematic view illustrating an example (in the case of the first person viewpoint) of the viewpoint switching screen.

On the viewpoint switching screen, as well as on the initial UI screen, the three-dimensional image display D1, the sectional image display D2, and the threshold setter D3 are displayed. In the instructor D4, icons, such as an icon for returning to the initial UI screen, an icon for switching the viewpoint, and an icon for storing the display content on the viewpoint switching screen, are displayed. Depending on the purpose of use, screens other than the three-dimensional image display D1 may not be displayed.

When displaying an object image, for example, in a case in which an object of an organ is examined from outside, the third person viewpoint is used, while, in a case in which the inside of an object of an organ is examined (in a display mode similar to that used with an endoscope), the first person viewpoint is used. This can enhance the ease of use.

While examining the inside of the organ from the first person viewpoint, the threshold is sequentially changed with the threshold setter D3. This can continuously display portions or the organ which are not continuous. By using the results obtained by continuously displaying portions of the organ while changing the threshold, data of the integrated portion of the organ can be created.

FIG. 9 shows schematic views illustrating examples of the display mode at the first person viewpoint.

In the case of the first person viewpoint, the movement of a virtual camera (viewpoint) can be made different in accordance with the angle between the advancing direction of the virtual camera and the surface of an object. As a result, the displaying of the object can be controlled the following manner.

For example, when the advancing direction of the virtual camera (viewpoint) and a line normal to a triangle mesh (triangle polygon) are substantially parallel with each other, the object is displayed in a state in which the virtual camera hits against the surface of the object and is pushed back. When the advancing direction of the virtual camera (viewpoint) and a line normal to a triangle mesh (triangle polygon) are substantially perpendicular to each other, the object is displayed in a state in which the virtual camera advances along the surface of the object.

With this operation, the inside of an object can be displayed in a mode similar to a situation, such where it is examined with an endoscope.

[Region Extracting Screen]

A region extracting screen is a screen to be displayed when a "region extract" menu in the instructor D4 is called on the initial UI screen or a screen be displayed when a specific key of the keyboard, for example, in the input unit 14 is being pressed.

On the region extracting screen, a continuous region of a displayed object can be extracted, identified, and displayed.

Figure 10:
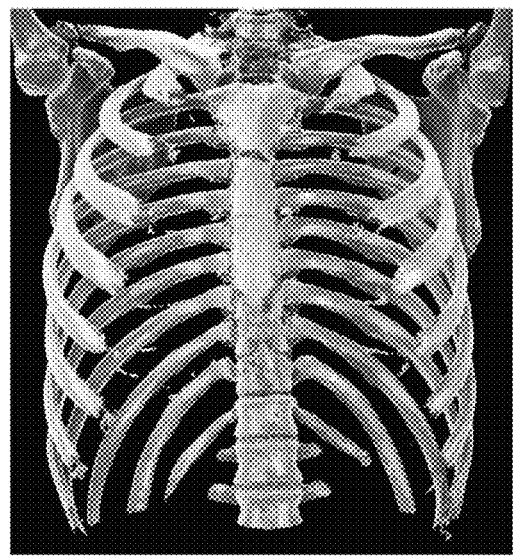
FIG. 10 is a schematic view illustrating a display example of surface data indicating a human chest cavity.
Figure 11:
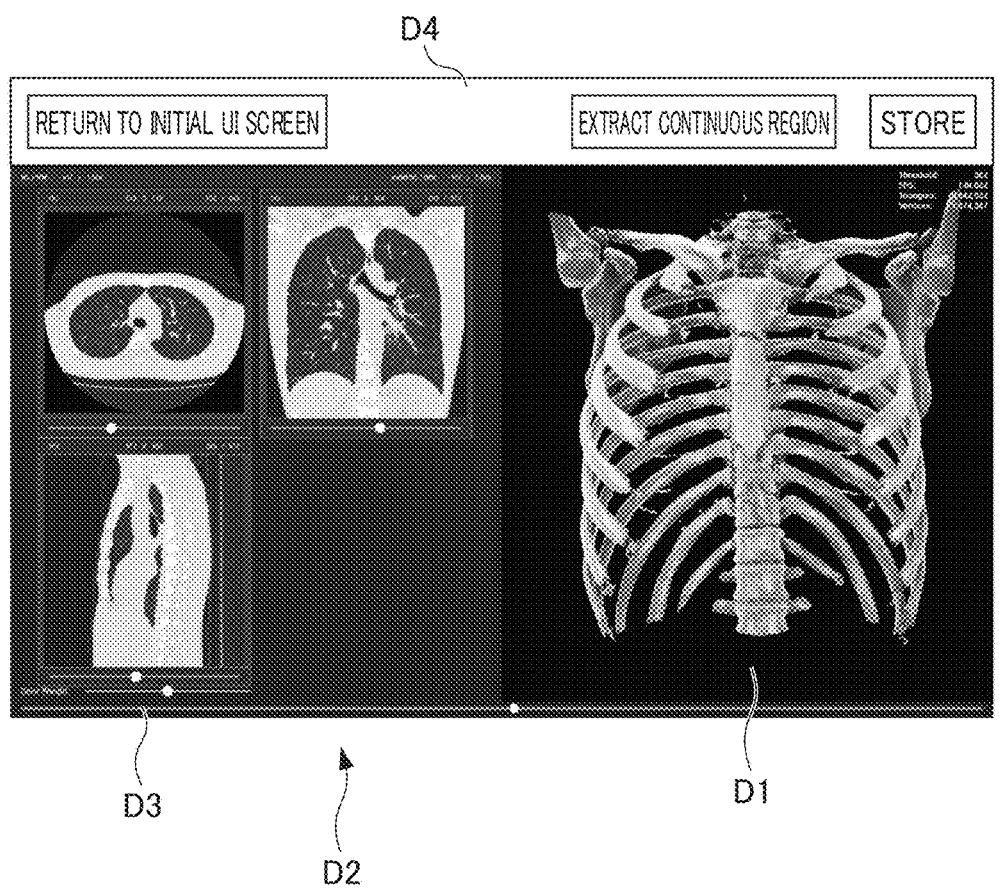
FIG. 11 is a schematic view illustrating an example of the region extracting screen.
Figure 12:
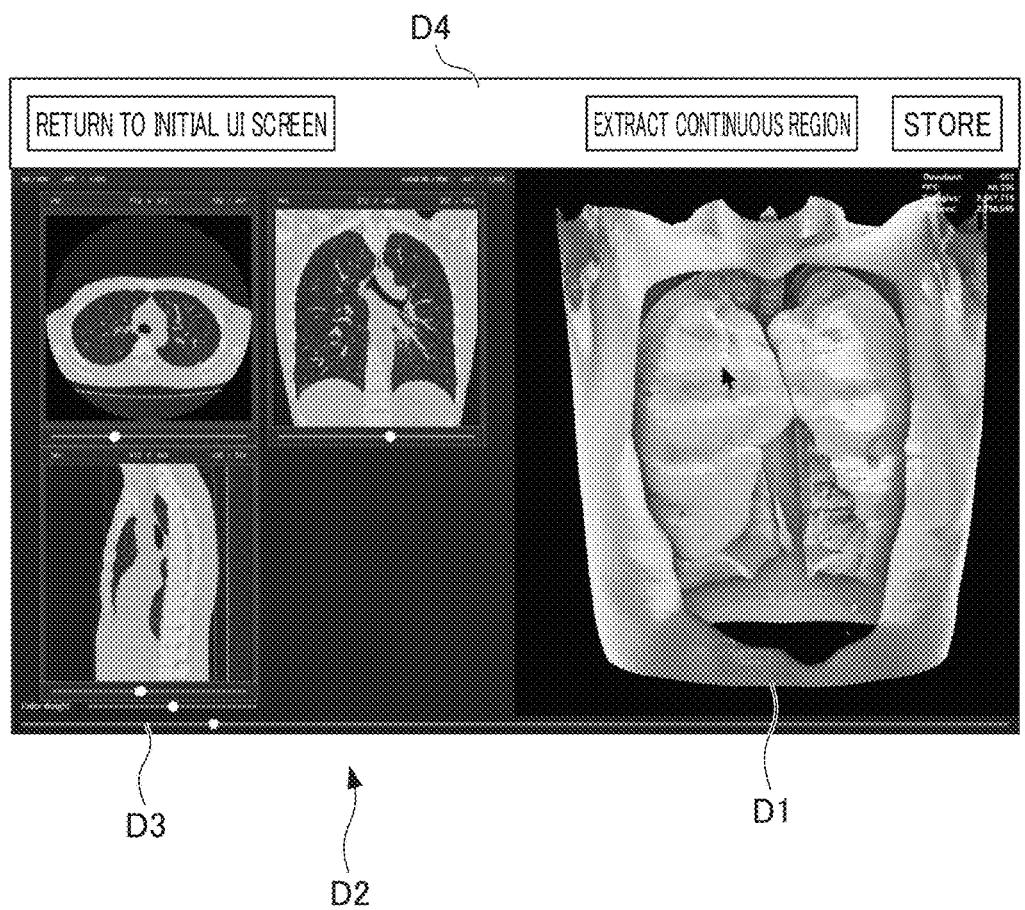
FIG. 12 is a schematic view illustrating that the display mode of an object displayed in the three-dimensional image display D1 is being changed by adjusting the threshold.
Figure 13:
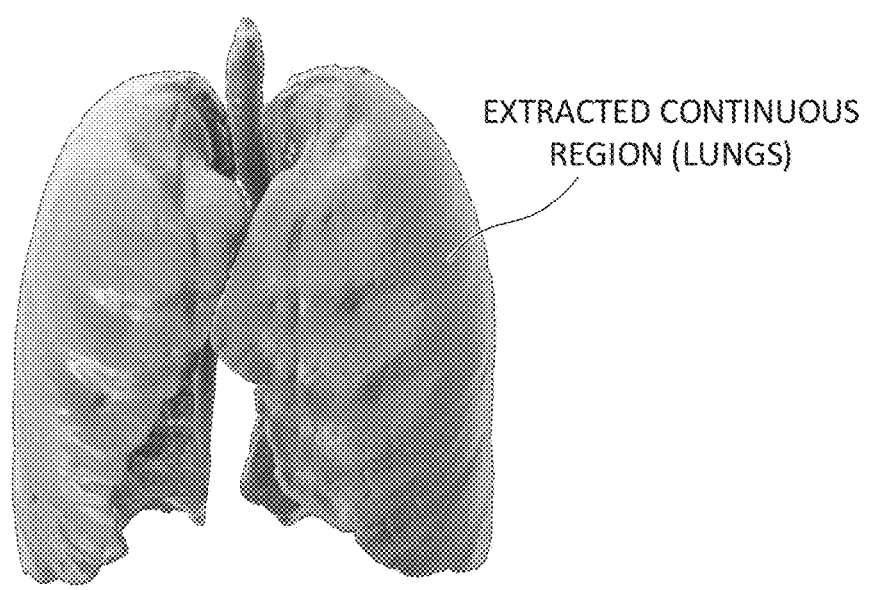
FIG. 13 is a schematic view illustrating a state in which part (lungs in this example) of an object displayed in the three-dimensional image display D1 is extracted as a continuous region.

FIG. 10 is a schematic view illustrating a display example of surface data indicating a human chest cavity. FIG. 11 is a schematic view illustrating an example of the region extracting screen. FIG. 12 is a schematic view illustrating that the display mode of an object displayed in the three-dimensional image display D1 being changed by adjusting the threshold. FIG. 13 is a schematic view illustrating a state in which part (lungs in this example) of an object displayed in the three-dimensional image display D1 is extracted as a continuous region.

On the region extracting screen, as well as on the initial UI screen, the three-dimensional image display D1, the sectional image display D2, and the threshold setter D3 are displayed. In the instructor D4, icons, such as an icon for returning to the initial UI screen, an icon for extracting a continuous region, and an icon for storing a result of extracting a continuous region on the region extracting screen, are displayed. Depending on the purpose of use, screens other than the three-dimensional image display D1 may not be displayed.

When extracting a continuous region from the object shown in FIG. 10, a user displays the object in the three-dimensional image display D1 of the region extracting screen shown in FIG. 11.

Then, by operating the threshold setter D3, the user adjusts the threshold so that part of the object to be extracted as a continuous region is displayed (see FIG. 12).

In a state in which part of the object to be extracted as a continuous region is displayed, the user specifies a point on this part of the object. Then, as shown in FIG. 13, the rendering processor 16b determines a region continuously extending from the specified point (triangle mesh) on surface data and displays the determined region in an identifiable manner (displaying the region in color, with edge enhancement, or with high luminance, for example). It may be possible that areas other than the determined region be not displayed or only the determined region be not displayed.

With the above-described operation, an integrated portion of an object can easily be extracted. For example, the integrated portion can be displayed so that a user can understand well how an organ is continuously formed, for example.

When extracting a continuous region, whether or not a region is regarded as a "continuous portion" can be determined based on whether this region is continuously displayed with a certain threshold.

The threshold to be used for extracting a "continuous portion" is not limited to a single threshold, but multiple thresholds may be used. For instance, a region regarded as a continuous portion based on one threshold and a region regarded as a continuous portion based on another threshold (for example, a heart which is continuous based on a first threshold and lungs which are continuous based on a second threshold) may be extracted, and these extracted regions may be maintained without any change even when the threshold is adjusted with the threshold setter D3 later.

[Illustration Display Screen]

An illustration display screen is a screen to be displayed when an "illustration" menu in the instructor D4 is called on the initial UI screen or a screen to be displayed when a specific key of the keyboard, for example, in the input unit 14 is being pressed.

On the illustration display screen, the complexity of a three-dimensional image can be eliminated with a technique for making a three-dimensional image look like two-dimensional animation (illustration) (such as cel shading or toon shading), and then, the resulting three-dimensional image can be displayed or printed.

Figure 14:
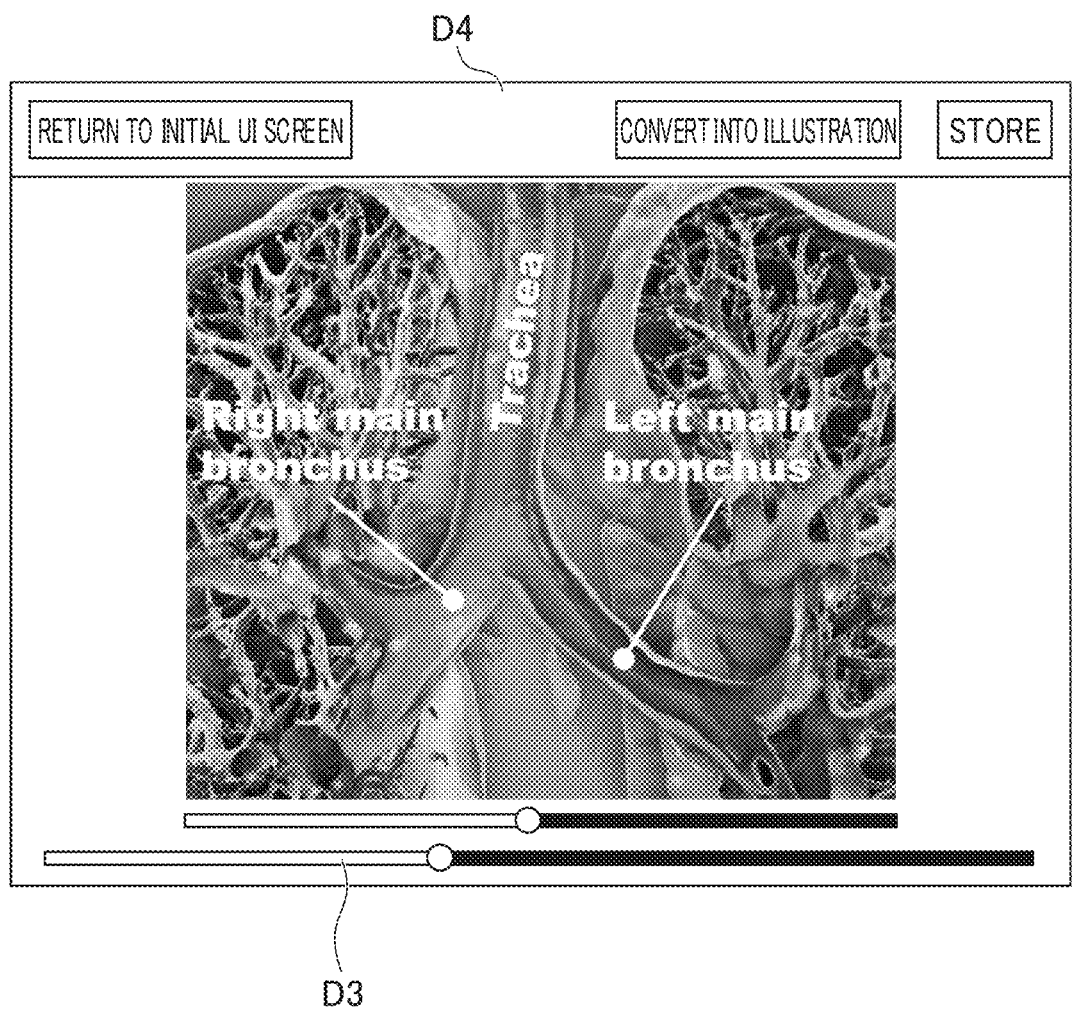
FIG. 14 is a schematic view illustrating an example of the illustration display screen (state in which a three-dimensional image is displayed).
Figure 15:
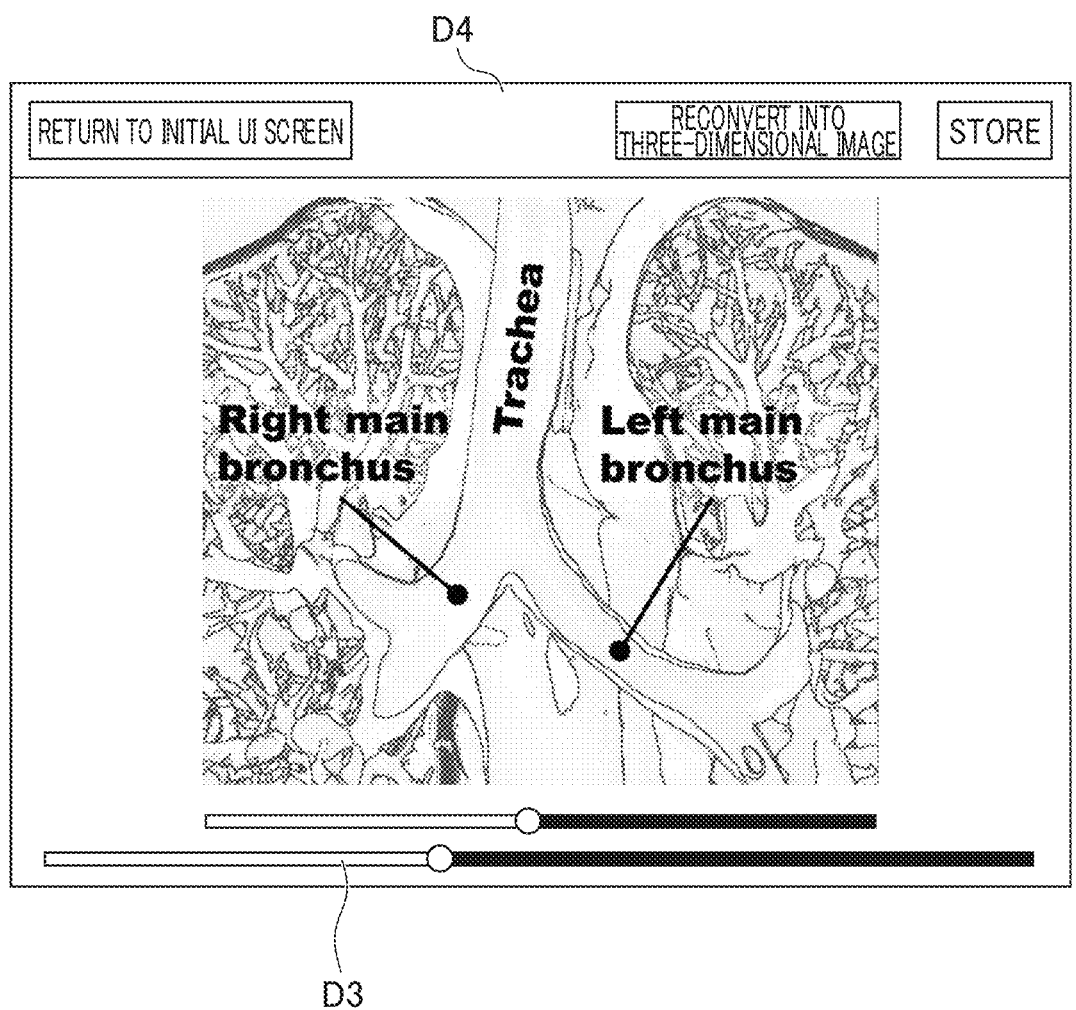
FIG. 15 is a schematic view illustrating an example of the illustration display screen (state in which an image is displayed as an illustration).

FIG. 14 is a schematic view illustrating an example of the illustration display screen (state in which a three-dimensional image is displayed). FIG. 15 is a schematic view illustrating an example of the illustration display screen (state in which an image is displayed as an illustration).

On the illustration display screen, the three-dimensional image display D1 and the threshold setter D3 are displayed. In the instructor D4, icons, such as an icon for returning to the initial UI screen, an icon for converting a three-dimensional image into an illustration (or an icon for reconverting an image as an illustration into a three-dimensional image), and an icon for storing a display result (image as an illustration) on the illustration display screen, are displayed. On the illustration display screen, as well as on the initial UI screen, the sectional image display D2 may be displayed, in which case, a sectional image can also be converted into an illustration. Depending on the purpose of use, screens other than three-dimensional image display D1 may not be displayed.

When a three-dimensional image is displayed or printed without being subjected to any processing (that is, when a three-dimensional image is displayed or printed two-dimensionally without any processing), the resulting image may become complicated and difficult to understand.

Especially in a situation, for example, where a doctor shows a CT image and gives an explanation about this to a patient, a considerable amount of information, which is not particularly necessary for the patient, is included in the CT image, which makes the CT image even more difficult to understand.

To address this issue, on the illustration display screen, by eliminating the complexity of a three-dimensional image with a technique for making the three-dimensional image look like two-dimensional animation (illustration) (such as cel shading or toon shading), the three-dimensional image is converted into a schematic image and is displayed.

If the three-dimensional image is displayed such that the surface and the inside of the object (the surface and the inside of a heart, for example) can be distinguished from each other, it becomes simple and easy to understand. Additionally, when text information, such as the names of individual parts of an object and comments, is displayed on the image, such text information is easier to identify on the image as an illustration (see FIG. 15) than on the three-dimensional image (see FIG. 14).

On medical records, for example, a three-dimensional image and an image as an illustration may be recorded together.

[Object Transformation Screen]

An object transformation screen is a screen to be displayed when a "transform" menu in the instructor D4 is called on the initial UI screen or a screen to be displayed when a specific key of the keyboard, for example, in the input unit 14 is being pressed.

On the object transformation screen, a result of applying some physical action to a displayed object, such as transforming or cutting the displayed object, can be simulated and displayed.

Figure 16:
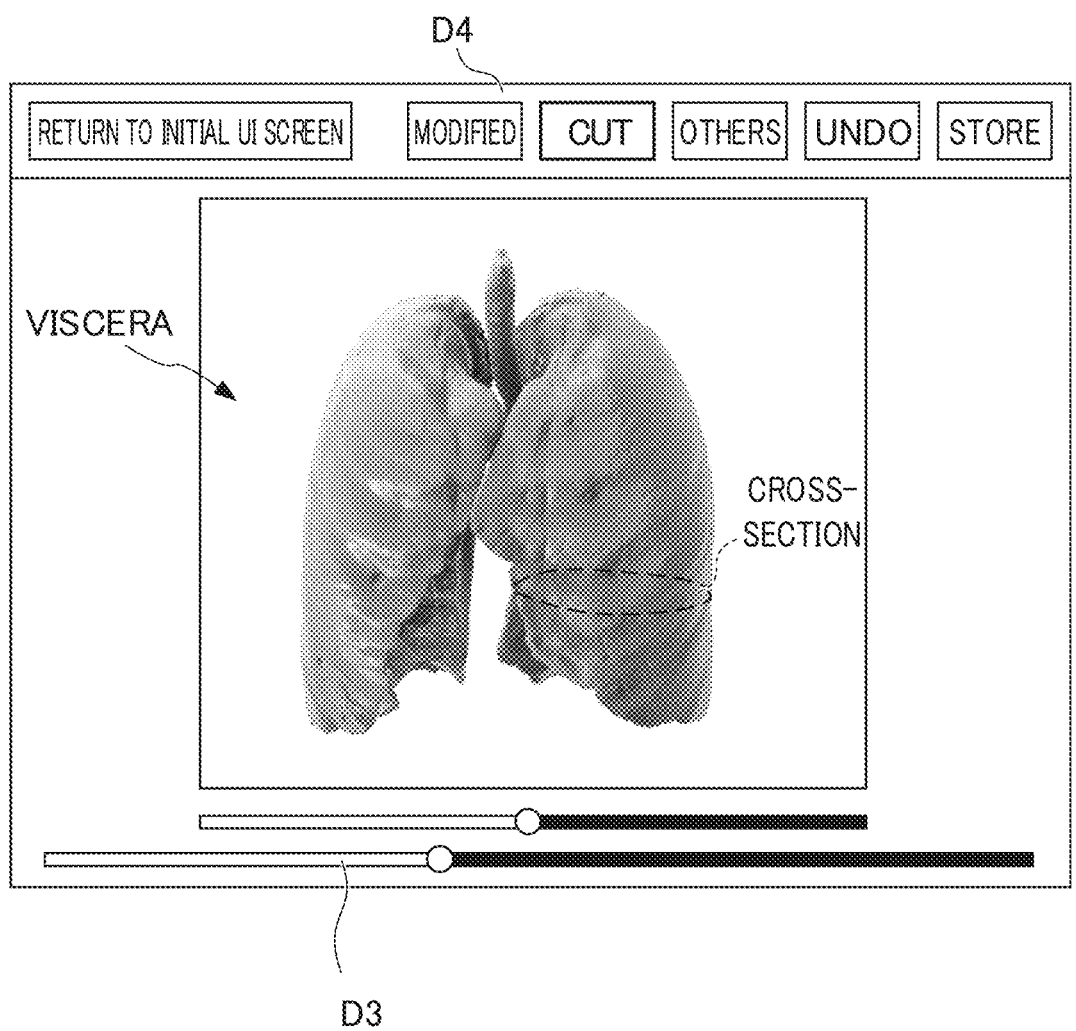
FIG. 16 is a schematic view illustrating an example of the object transformation screen.

FIG. 16 is a schematic view illustrating an example of the object transformation screen.

On the object transformation screen, the three-dimensional image display D1 and the threshold setter D3 are displayed. In the instructor D4, icons, such as an icon for returning to the initial UI screen, an icon for transforming an object, an icon for cutting an object, an icon for applying other physical action to an object, an icon for undoing operation, and an icon for storing a result of performing operation on the object transformation screen as an image, are displayed.

Since the image processing device 1 handles surface data constituted by continuous triangle meshes, it can easily perform simulation including the application of physical action, such as transformation of an object. If a new surface is generated due to the transformation of an object, for example, the image processing device 1 can determine the positions of the vertices of triangle meshes by using the vertex-position determining table, so that surface data indicating the surface of the object can be generated at high speed.

[Operation]

The operation of the image processing device 1 will now be described below.

[Object Display Processing]

Figure 17:
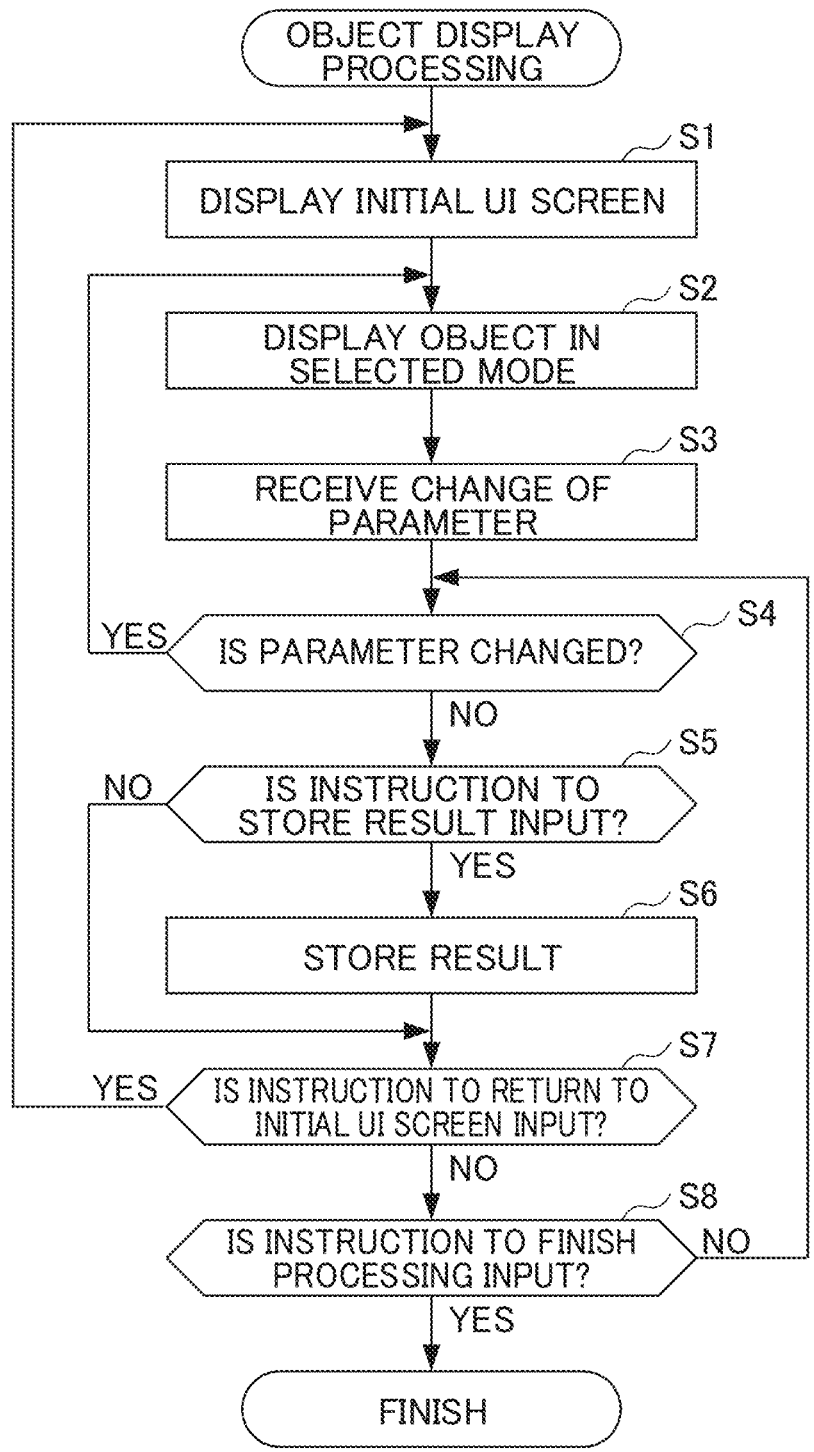
FIG. 17 is a flowchart illustrating a procedure of object display processing executed by the image processing device 1.

FIG. 17 is a flowchart illustrating a procedure of object display processing executed by the image processing device 1.

Object display processing is started in response to receiving input of an instruction to execute object display processing via the input unit 14.

When object display processing is started, in step S1, the UI controller 11a displays the initial UI screen. On the initial UI screen, the selecting of object data to be displayed and the selecting of a menu of a display mode, for example, are received.

In step S2, the UI controller 11a displays an object in the selected display mode. For example, the UI controller 11a shifts the UI screen to a corresponding display screen, such as the physical-quantity measuring screen, the position display screen, or the viewpoint switching screen, in response to the selecting of an icon of one of the various display modes. When the UI screen is shifted to the display screen of a certain display mode, the object is displayed initially in accordance with a default parameter (such as a default viewpoint or a default threshold).

In step S3, the UI controller 11a shifts to a state in which it can receive a change of the parameter (such as the viewpoint, threshold, position of a cross section) from a user.

In step S4, the rendering processor 16b determines whether the parameter is changed by the user.

If the parameter is changed by the user, the determination result of step S4 becomes YES, and the process returns to step S2. Then, the displaying of the object is updated in accordance with the changed parameter. To update the displaying of the object, the vertex-position determining table is used, thereby achieving fast processing.

If the parameter is not changed by the user, the determination result of step S4 becomes NO, and the process proceeds to step S5.

In step S5, the UI controller 11a determines whether an instruction to store the result displayed on the display screen is input from the user.

Is an instruction to store the result displayed on the display screen is not input, the determination result of step S5 becomes NO and the process proceeds to step S7.

If an instruction to store the result displayed on the display screen is input, the determination result of step S5 becomes YES, and the process proceeds to step S6.

In step S6, the data manager 11b stores the result displayed on the display screen in the storage 17.

In step S7, the UI controller 11a determines whether an instruction to return to the initial UI screen is input from the user.

If an instruction to return to the initial UI screen is input from the user, the determination result of step S7 becomes YES, and the process returns to step S1.

If an instruction to return to the initial UI screen is not input from the user, the determination result of step S7 becomes NO, and the process proceeds to step S8.

In step S8, the UI controller 11a determines whether an instruction to finish object display processing is input.

If an instruction to finish object display processing is not input, the determination result of step S8 becomes NO, and the process returns to step S4.

If an instruction to finish object display processing is input, the determination result of step S8 becomes YES, and object display processing is completed.

By executing the above-described processing, the image processing device 1 can implement high-speed displaying of surface data generated from volume data in various display modes in which an object can be transformed and measured, for example.

The image processing device 1 is, thus able to visualize a three-dimensional image appropriately.

First Modified Example

In the above-described embodiment, the vertex-position determining table has been explained through illustration of the mode shown in FIG. 2. However, the vertex-position determining table is not restricted to this mode.

That is, various modifications may be made to the vertex-position determining table if it is possible to easily identify on which edge a vertex of a triangle mesh is present. For example, in accordance with the number of edges (two for two-dimensional volume data and three for three-dimensional volume data) extending from a vertex of volume data in a predetermined direction (each of the top-bottom direction, left-right direction, and front-back direction), these edges may be treated as a group. This makes it possible to quicken the speed in identifying on which edge a vertex of a triangle mesh is present.

FIG. 18 is a schematic diagram illustrating a modified example of the vertex-position determining table.

For the sake of simple description, it is assumed that, in FIG. 18, two edges extend from a vertex of volume data in a predetermined direction (two-dimensional volume data).

As shown in FIG. 18, in this modified example, in the first row of the vertex-position determining table, the number for identifying the edge of a voxel representing volume data is stored.

In the second row of the vertex-position determining table, a first flag indicating whether or not a vertex of a triangle mesh is present on an individual edge in the first row (if a vertex is present, the first flag indicates "1", and if no vertex is present, the first flag indicates "0") is stored. Whether a vertex of a triangle mesh is present on an edge can be determined based on whether the values of voxels located at both ends of the edge have a predetermined difference (which is a value greater than or equal to a threshold used for determining whether the edge between voxels is a surface).

In the vertex-position determining table in this modified example, two edges are treated as one pair. That is, two edges are set as a pair in ascending order of the edge number, and a second flag is set for each pair.

More specifically, in the third row of the vertex-position determining table, the result of adding the values of the first flag for each pair of two edges, which are set in ascending order of the edge number, is stored as a second flag.

In the fourth row of the vertex-position determining table, the hash value determined based on the number for identifying the edge in the first row and the second flag in the third row for this edge is stored. For a pair of the 2n-th and the (2n+1)-th edge (n is a natural number), for example, the hash value in the fourth row is calculated by adding the hash value of the pair of the 2 (n−1)-th edge and the (2(n−1)−1)-th edge and the second flag of the 2(n−1)-th edge and (2(n−1)+1)-th edge. The hash value of the pair of the 0-th edge and the first edge is the same value as the second flag of this pair. In this manner, the hash values in the vertex-position determining table can be calculated by the above-described sequential addition processing. Hence, as a result of the image processor 16 executing this processing, high-speed processing can be implemented.

In the fifth row of the vertex-position determining table, the number for identifying each pair of two edges, which are set in ascending order of the edge number, is stored. The number for identifying a pair of two edges represents the number for identifying the vertex of volume data (Voxel ID (it is however indicated as "Pixel ID" in FIG. 18 since the vertex-position determining table in FIG. 18 is an example for two-dimensional volume data).

To identify on which edge a vertex of a triangle mesh is present from the above-described vertex-position determining table, the hash value in the fourth row is checked. This makes it possible to easily identify on which edge the m-th (m is an integer of 0 or greater) vertex is present.

In the vertex-position determining table, the hash values in the fourth row are discontinuous. For a pair of two edges where the hash value becomes discontinuous, a vertex of a triangle mesh is present on both of the two edges, which are set in ascending order of the edge number.

When referring to the vertex (for example, the k-th vertex (k is a natural number)) of a triangle mesh corresponding to a discontinuous hash value among the hash values set in the fourth row of the vertex-position determining table, it can be determined that this vertex is present on the larger number of edge between the two edges of the pair to which the (k−1)-th vertex, which is smaller than the k-th vertex by one, belongs.

By using the above-described type of vertex-position determining table, even when the number of edges in volume data is increased, a smaller amount of data can be stored. Then, it is still possible to identify on which edge a triangle mesh is present.

Second Modified Example

In the above-described embodiment, when displaying object data (surface data), the positions of the vertices of the triangle meshes forming the surface data are determined based on the threshold set by the threshold setter D3. Then, a specific color (black or white, for example) is added to the entire surface represented by a set of the triangle meshes. The object is displayed in this manner.

In this case, it is possible to display objects having considerably different voxel values (such as bones and blood vessels) together by setting one threshold, the surfaces can be displayed by relatively simple processing, which enhances the ease of use.

However, if objects having considerably different voxel values are displayed together by setting one threshold, the surfaces of these objects are displayed in the same color since the same threshold is set for the objects.

It may be thus difficult to distinguish the surfaces of different objects from each other, depending on conditions, such as the viewpoint and the position of a cross section.

To address this issue, in this modified example, when adding color to the surface of an object, the value of a voxel adjacent to a vertex of a triangle mesh is checked, and the color of a voxel selected in accordance with a set condition (hereinafter called the "coloring-reference-voxel selection condition") is set as the color of the vertex of the triangle mesh. Then, the object is displayed.

This makes it possible to correct the color of the surface of an object by reflecting the attributes of the object (the values of the internal voxels). Hence, when objects having considerably different voxel values are extracted with one threshold, the surfaces of these different objects can be displayed in a mode in which they can be easily distinguished from each other. Additionally, within the same object, too, colors corresponding to different voxel values can be distinguished from each other.

Figure 19:
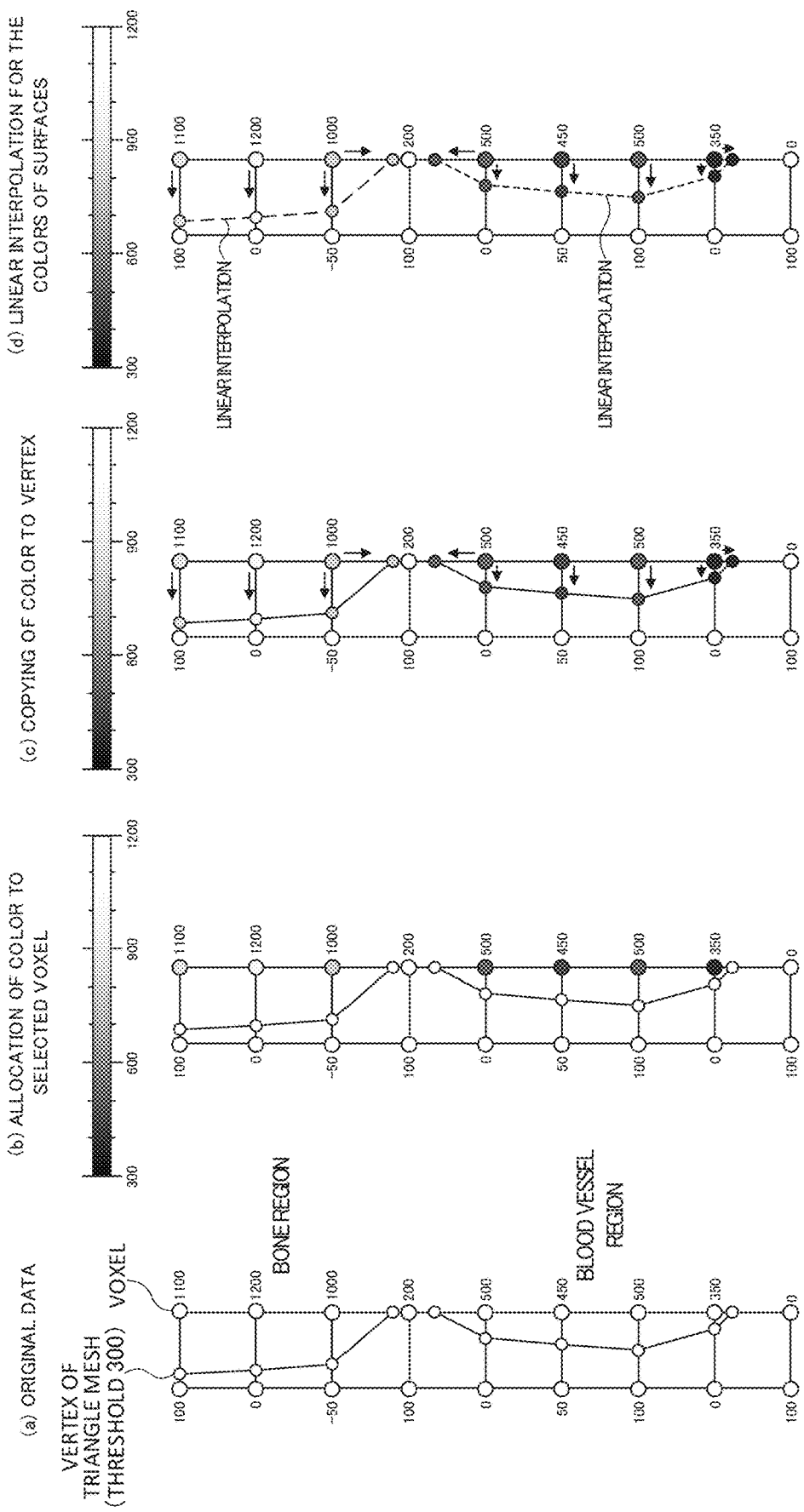
FIG. 19 shows schematic diagrams illustrating a color correction method for the surfaces of objects in this modified example.

FIG. 19 shows schematic diagrams illustrating a color correction method for the surfaces of objects in this modified example.

For the sake of description, FIG. 19 illustrates two-dimensional volume data whose surface is represented by line segments by way of example. In the case of three-dimensional volume data, the surface is represented by triangle meshes, and correction can be performed similarly for the individual vertices of the triangle meshes. In the example in FIG. 19, as a voxel to be selected based on the coloring-reference-voxel selection condition, one of the voxels which sandwich a vertex of a triangle mesh (the internal voxel of the object, in this example) is selected.

In FIG. 19, the individual points shown in "(a) Original data" represent voxels, and the numerical value appended to each point indicates the value of the corresponding voxel.

In the example in FIG. 19, the voxels belonging to a "bone" region are distributed around the value of about 1200, while the voxels belonging to a "blood vessel" region are distributed around the value of about 400.

In this case, when the threshold is set to 1000, the bone region is extracted with high precision, but the blood vessel region is not extracted.

If the threshold is set to 300, the bone region and the blood vessel region are both extracted. However, the extracted bone region becomes slightly rounder than when the threshold is set to 1000.

Nevertheless, even though the bone region becomes slightly rounder than when the threshold is set to 1000, if the difference is such a degree as to that a vertex of a triangle mesh is shifted to a different position of the same side of the triangle mesh, it is still desirable to display the surfaces of the bone region and the blood vessel region together by setting one threshold.

In this modified example, between voxels which sandwich a vertex of a triangle mesh, a color is allocated to the voxel located on the internal side of the object, and the color of this voxel is copied to the vertex of the triangle mesh.

This will be discussed more specifically. As shown in "(a) Original data" in FIG. 19, when the threshold is set to 300, the regions having voxel (pixel) values of 300 or greater are defined as those located on the internal side of the object.

As shown in "(b) Allocation of color to selected voxel" in FIG. 19, between the voxels which sandwich a corresponding vertex of a triangle mesh, a color corresponding to a value of the object is allocated to the voxel on the internal side of the object (that is, the voxel having a larger value than the set threshold).

Then, as shown in "(c) Copying of color to vertex" in FIG. 19, the color assigned to the voxel on the internal side of the object is copied to the corresponding vertex of the triangle mesh.

Then, as shown in "(d) Linear interpolation for the colors of surfaces" in FIG. 19, based on the colors of the vertices of the triangle meshes, the color of each portion (surface) between vertices is linearly interpolated, thereby adding the resulting colors to the surfaces of the object.

FIG. 20 shows schematic views illustrating an example of a comparison result obtained by displaying different objects together with one threshold according to the color correction method of this modified example. In FIG. 20, an example in which objects are displayed together using the original technique (technique of the first embodiment) of the invention of this application and an example in which objects are displayed together using the technique of the present modified example are shown by comparison.

As shown in FIG. 20, by using the color correction method of the second modified example, even though regions having considerably different voxel values are extracted with one threshold, they can be displayed as objects whose surfaces are expressed in somewhat different colors because the values of voxels inside the objects are reflected on the surfaces.

If a region having voxel values that are smaller than a set threshold is defined as that located on the internal side of the object, a color is allocated to the voxel having a smaller value than the threshold, and the color of this voxel is copied to the corresponding vertex of a triangle mesh.

Third Modified Example

According to the above-described second modified example, even when regions having considerably different voxel values are extracted with one threshold, they can be displayed as objects whose surfaces are expressed in somewhat different colors.

If, however, the boundary between objects represented by volume data is not clearly expressed between adjacent voxels, the colors of the different objects may partially become similar or the color of the same object may not become uniform but be expressed like a mosaic or striped pattern, as illustrated in FIG. 20.

To address this issue, in the present modified example, the color correction method for the surfaces of objects in the second modified example is modified to implement the following display technique. Even for volume data representing objects whose boundary is not clearly expressed between adjacent voxels, regions having considerably different voxel values extracted with one threshold can be displayed in different colors.

FIG. 21 shows schematic diagrams illustrating a color correction method for the surfaces of objects of volume data whose boundary is not clearly expressed between adjacent voxels. In FIG. 21, "(a) Colors of surfaces subjected to linear interpolation" shows a state in which the color correction method illustrated in FIG. 19 is performed on the original volume data (state of "(d) Linear interpolation for the colors of surfaces").

As illustrated in "(a) Colors of surfaces subjected to linear interpolation" in FIG. 21, if a voxel having the intermediate value between the value of the internal voxel and that of the external voxel of an object is present at a boundary with another object, because of the presence of this voxel having the intermediate value, the surfaces of the different objects are partially expressed by similar colors.

In this modified example, as a voxel to be selected based on the coloring-reference-voxel selection condition, one of the voxel sets which sandwich a vertex of a triangle mesh is selected, and then, the voxel having the largest (or the smallest) value of the selected voxel set is selected.

This will be discussed more specifically. In the voxel set in the first row in the example of "(a) Colors of surfaces subjected to linear interpolation" in FIG. 21, if the voxels (pixels) are arranged in order of 100, 1100, 1200, for example, the boundary between objects is clearly expressed between the adjacent voxels. In actuality, however, the voxels are arranged in order of 100, 350, 1100 with the presence of the voxel having an intermediate value of 350 between the internal voxel having a value of 1100 and the external voxel having a value of 100.

Because of the presence of such a voxel having an intermediate value, the surfaces of the bone region and the blood vessel region shown in "(a) Colors of surfaces subjected to linear interpolation" in FIG. 21 are partially expressed by similar colors.

In contrast, in "(b) Color correction method for the surfaces of objects in the third modified example" in FIG. 21, in the voxel set in the first row, not only the voxel having a value of 350 next to the vertex of a triangle mesh, the voxel having a value of 1100, which is next to the vertex but one, are selected based on the coloring-reference-voxel selection condition.

Then, between the voxel having a value of 350 and the voxel having a value of 1100 adjacent to the vertex of the triangle mesh, the voxel having the larger value is selected and the color corresponding to the voxel having a value of 1100 is copied to the vertex of the triangle mesh.

The above-described processing is executed on the vertices of the individual triangle meshes in the row direction or the column direction, so that the attributes of the object (values of the internal voxels) are explicitly reflected. The colors of the surfaces are corrected in this manner.

FIG. 22 shows schematic views illustrating an example of a comparison result obtained by displaying different objects together with one threshold according to the color correction method of this modified example. In FIG. 22, an example in which objects are displayed together using the original technique (technique of the first embodiment) of the invention of this application and an example in which objects are displayed together using the technique of the present modified example are shown by comparison.

As shown in FIG. 22, by using the color correction method of the third modified example, even for voxel data representing objects whose boundary is not clearly expressed between adjacent voxels, when regions having considerably different voxel values are extracted with one threshold, they can be displayed as objects whose surfaces are expressed in different colors because the values of voxels inside the objects are more intensely reflected on the surfaces.

Fourth Modified Example

In the example shown in FIG. 21 according to the third modified example, as a voxel to be selected based on the coloring-reference-voxel selection condition, up to two voxels adjacent to a vertex of a triangle mesh in one direction are selected by way of example. However, more adjacent voxels may be selected. Moreover, in addition to selecting voxels adjacent to a vertex of a triangle mesh in one direction, voxels around a vertex of a triangle mesh may be selected.

FIG. 23 shows schematic diagrams illustrating an example of a color correction method to select voxels around a vertex of a triangle mesh as voxels to be selected based on the coloring-reference-voxel selection condition.

FIG. 23 shows an example in which voxels to be selected based on the coloring-reference-voxel selection condition are further extended in the following manner. After two voxels adjacent to a vertex of a triangle mesh in one direction are selected based on the coloring-reference-voxel selection condition as in the third modified example, one voxel in a direction and one in another direction intersecting with (perpendicular to, in this example) the selected voxel which is next to the vertex but one are selected.

As in the example in "(a) Part of the color correction method for the surfaces of objects in the third modified example" in FIG. 23, even with the use of the color correction method in the third modified example, especially for volume data representing objects whose boundary is not clearly expressed between adjacent voxels, a voxel to be referred to does not have a value of a voxel inside the object. This causes some defects, such as the appearance of a striped pattern (or a discontinuous color at a corner) on the surface of an object. Hence, there is still room for improvement to display the surface of an object more smoothly.

In this modified example, voxels to be selected are extended as follows. After two voxels adjacent to a vertex of a triangle mesh in one direction are selected, one voxel in a direction and one in another direction intersecting with (perpendicular to) the selected voxel next to the vertex but one are selected.

This will be explained more specifically. In FIG. 23, in the example of "(b) In the process of executing the color correction method for the surfaces of objects in the fourth modified example", the vertex of a triangle mesh in the second row is focused. Regarding this vertex, as shown in the diagram on the left side, the two voxels adjacent to this vertex on the right side in the second row and the two voxels adjacent to the voxel at the right edge of the second row in the top and bottom directions are selected. Among these voxels, the voxel having the largest value, which is 1200, is selected, and the color of this voxel is copied to the focused vertex of the triangle mesh.

Then, the vertex of the triangle mesh in the third row in the example of "(b) in the process of executing the color correction method for the surfaces of objects in the fourth modified example" in FIG. 23 is focused. Regarding this vertex, too, as shown in the diagram on the right side, the two voxels adjacent to this vertex on the right side in the third row and the two voxels adjacent to the voxel at the right edge of the third row in the top and bottom directions are selected. Among these voxels, the voxel having the largest value, which is 1200, is selected, and the color of this voxel is copied to the focused vertex of the triangle mesh.

As a result of executing the above-described processing, as shown in the example in "(c) Part of the color correction method for the surfaces of objects in the fourth modified example" in FIG. 23, the color corresponding to the voxel having the value of 1200 is copied to the vertices of all the triangle meshes on the surface of the object located near the voxel having the value of 1200.

Hence, compared with the example in "(a) Color correction method for the surfaces of objects in the third modified example (partially extracted)" in FIG. 23, a striped pattern (or a discontinuous color at a corner) is less likely to appear on the surface of the object.

That is, by using the color correction method of the fourth modified example, it is possible to prevent the appearance of an abnormal color on the surface of an object and thus to display the surface of the object more smoothly.

FIG. 24 shows schematic views illustrating an example of a comparison result obtained by displaying different objects together with one threshold according to the color correction method of the present modified example. In FIG. 24, an example in which objects are displayed together using the original technique (technique of the first embodiment) of the invention of this application and an example in which objects are displayed together using the technique of the present modified example are shown by comparison.

As shown in FIG. 24, by using the color correction method of the fourth modified example, even for voxel data representing objects whose boundary is not clearly expressed between adjacent voxels, the value of a more suitable voxel among the voxels inside each object is reflected on the surface. Thus, even when regions having considerably different voxel values are extracted with one threshold, the objects whose surfaces are expressed in different colors can be displayed more smoothly.

The image processing device 1 configured as described above includes the UI controller 11a and the rendering processor 16b.

The rendering processor 16b obtains, from volume data constituted by multiple points, each point having a value, surface data representing the shape of a surface. The shape of the surface is defined by the magnitude of each of the values.

The UI controller 11a sets a threshold for the values to determine whether to display the surface data.

The rendering processor 16b determines an intersecting point at which a straight line passing through a position set as a viewpoint and a point specified by a user intersects with the shape of the surface which is to be displayed in accordance with the threshold.

Based on a plane passing through the intersecting point, the rendering processor 16b controls the displaying of the shape of the surface represented by the surface data.

This makes it passible to display surface data generated from volume data in various display modes at high speed.

The image processing device 1 is thus able to visualize a three-dimensional image appropriately.

The rendering processor 16b obtains the surface data from the volume data by referring to table data indicating edge information, a flag, and vertex identification information associated with each other. The edge information is used for identifying an edge of a voxel forming the volume data. The flag indicates whether a vertex of a triangle mesh forming the surface data is present on the edge. The vertex identification information is used for identifying a vertex of the triangle mesh which is identified based on the edge information and the flag.

This makes it possible to execute even higher-speed processing for obtaining surface data from volume data.

The rendering processor 16b displays the surface data located on one side of the plane passing through the intersecting point and does not display the surface data located on the other side of the plane.

This makes it possible to easily generate a sectional image.

In response to a specific operation performed on displayed surface data, the rendering processor 16b calculates a physical quantity corresponding to the specific operation, based on the surface data.

With this configuration, in response to an operation on the displayed surface data, a physical quantity of an object represented by the surface data can be measured.

When a voxel on the surface data is specified, the rendering processor 16b displays a sectional image passing through the specified voxel.

With this configuration, when it is desired to check a specific part of an object, the voxel to be checked can easily be recognized.

In response to a user operation, the rendering processor 16b switches between a first display mode and a second display mode. The first display mode is a mode in which an object represented by the volume data is viewed from outside of the object. The second display mode is a mode in which the object is viewed from inside of the object.

This makes it possible to switch the viewpoint to a suitable viewpoint in accordance with whether an object is viewed from outside or inside, thereby enhancing the ease of use when displaying the object.

The UI controller 11a sets a first threshold and a second threshold to determine whether to display surface data.

The rendering processor 16a controls the displaying of the surface data, based on the corresponding values determined by the set first and second thresholds.

This makes it possible to set a variety of thresholds to suitably represent surface data.

In response to an operation performed on a specific point on displayed surface data, the rendering processor 16b extracts a portion continuous from the specified point based on the surface data.

This makes it possible to easily extract an integrated portion of an object represented by surface data and to display the extracted integrated portion so as to easily understand how an organ is continuously formed, for example.

In response to a user instruction, the rendering processor 16b converts the surface data which is displayed into a second-dimensional image as an illustration and displays the converted second-dimensional image.

This makes it possible to eliminate the complexity of an image and to display a schematically illustrated easy-to-understand image.

When one threshold is set, the rendering processor 16b displays the surfaces of different objects, which are objects represented by volume data and are to be displayed based on the set threshold. The surface of each of the different objects is displayed in a color based on a value of a voxel located on an internal side of the corresponding object.

With this configuration, even when regions having considerably different voxel values are extracted with one threshold, they can be displayed as objects whose surfaces are expressed in different colors. Additionally, within the same object, colors corresponding to different voxel values can be distinguished from each other.

The present invention is not to be limited to the above-described embodiment. Various changes, modifications, etc. are also covered by the present invention as long as such changes, modifications, etc. fall in a range in which the object of the present invention can be achieved.

That is, the present invention is applicable to various electronic devices having an image processing function.

The processing sequence described above can be executed by hardware, and can also be executed by software.

In other words, the functional configurations of FIG. 1 is merely an illustrative example, and the present invention is not particularly limited thereto. More specifically, the types of functional blocks employed to realize the above-described functions are not particularly limited thereto, so long as the image processing device 1 can be provided with the functions enabling the aforementioned processing sequence to be executed in its entirety.

A single functional block may be configured by a single piece of hardware, a single installation of software, or a combination thereof.

The functional configurations the present embodiment are realized by a processor executing arithmetic processing, and processors that can be used for the present embodiment include a unit configured by a single unit of a variety of single processing devices such as a single processor, multi-processor, multi-core processor, etc., and a unit in which the variety of processing devices are combined with a processing circuit such as ASIC (Application Specific Integrated circuit) or FPGA (Field-Programmable Gate Array).

In the case of having the series of processing executed by software, the program constituting this software is installed from a network or recording medium to a computer or the like.

The computer may be a computer equipped with dedicated hardware. In addition, the computer may be a computer capable of executing various functions, e.g., a general purpose personal computer, by installing various programs.

The storage medium containing such a program can not only be constituted by the removable medium distributed separately from the device main body for supplying the program to a user, but also can be constituted by a storage medium or the like supplied to the user in a state incorporated in the device main body in advance. The removable medium is composed of, for example, a magnetic disk (including a floppy disk), an optical disk, a magnetic optical disk, or the like. The optical disk is composed of, for example, a CD-ROM (Compact Disk-Read Only Memory), a DVD (Digital Versatile Disk), Blu-ray (Registered Trademark) Disc or the like. The magnetic optical disk is composed of an MD (Mini Disk) or the like. The storage medium supplied to the user in a state incorporated in the device main body in advance is constituted by, for example, the ROM in which the program is recorded or a semiconductor memory, etc. included in the storage unit 20B.

The embodiments of the present invention described above are only illustrative, and are not to limit the technical scope of the present invention. The present invention can assume various other embodiments. Additionally, it is possible to make various modifications thereto such as omissions or replacements within a scope not departing from the spirit of the present invention. These embodiments or modifications thereof are within the scope and the spirit of the invention described in the present specification, and within the scope of the invention recited in the claims and equivalents thereof.

REFERENCE SIGNS LIST

1 image processing device, 11 CPU (Central Processing Unit), 11a user interface controller (UI controller), 11b data manager, 12 ROM (Read Only Memory), 13 RAM (Random Access Memory), 14 input unit, 15 display unit, 16 image processor, 16a object data obtainer, 16b rendering processor, 17 storage, 18 communication unit

The invention claimed is:

1. An image processing device comprising:
at least one hardware processor which is configured to:
obtain, from volume data constituted by a plurality of points, each point having a value, surface data representing a shape of a surface, the shape of the surface being defined by a magnitude of each of the values;
set a threshold for the values, the threshold being used to determine whether to display the surface data;
determine an intersecting point at which a straight line passing through a position set as a viewpoint and a point specified by a user intersects with the shape of the surface which is to be displayed in accordance with the threshold; and
control, based on a plane passing through the intersecting point, displaying of the shape of the surface represented by the surface data,
wherein, when the surface data representing the shape of the surface is updated as a result of the threshold being changed, at least one hardware processor determines the intersecting point at which the straight line passing through the position set as the viewpoint and the point specified by the user intersects with the updated shape of the surface, and
wherein, based on a plane passing through the intersecting point on the updated shape of the surface, the at least one hardware processor controls the displaying of the shape of the surface represented by the surface data.

2. The image processing device according to claim 1, wherein the at least one hardware processor obtains the surface data from the volume data by referring to table data indicating edge information, a flag, and vertex identification information associated with each other, the edge information being used for identifying an edge of a voxel forming the volume data, the flag indicating whether a vertex of a triangle mesh forming the surface data is present on the edge, the vertex identification information being used for identifying a vertex of the triangle mesh, the vertex being identified based on the edge information and the flag.

3. The image processing device according to claim 1, wherein, when displaying the surface data, the at least one hardware processor controls display so that the surface data located on one side of the plane passing through the intersecting point is displayed and the surface data located on the other side of the plane is not displayed.

4. The image processing device according to claim 1, wherein the at least one hardware processor is further configured to:
calculate, in response to a specific operation performed on the displayed surface data, a physical quantity corresponding to the specific operation, based on the surface data.

5. The image processing device according to claim 1, wherein, when a voxel on the surface data is specified, the at least one hardware processor displays a sectional image passing through the specified voxel.

6. The image processing device according to claim 1, wherein, in response to a user operation, the at least one hardware processor switches between a first display mode and a second display mode, the first display mode being a mode in which an object represented by the volume data is viewed from outside of the object, the second display mode being a mode in which the object is viewed from inside of the object.

7. The image processing device according to claim 1, wherein:
the at least one hardware processor sets a first threshold and a second threshold, the first and second thresholds being used to determine whether to display the surface data; and
the at least one hardware processor controls the displaying of the surface data, based on the values determined by the set first and second thresholds.

8. The image processing device according to claim 1, wherein the at least one hardware processor is further configured to:
extract, in response to an operation performed on a specific point on the displayed surface data displayed, a portion continuous from the specified point based on the surface data.

9. The image processing device according to claim 1, wherein, in response to a user instruction, the at least one hardware processor converts the surface data, which is displayed, into a two-dimensional image as an illustration and displays the converted second-dimensional image, the converted two-dimensional image being able to be subjected to a three-dimensional operation including rotation.

10. The image processing device according to claim 1, wherein, when the threshold, which is a single threshold, is set, the at least one hardware processor displays the surfaces of different objects, which are objects represented by the volume data and are to be displayed based on the single threshold, the surface of each of the different objects being displayed in a color which is uniquely determined by a value of a voxel located on an internal side of the corresponding object, regardless of a direction of a viewpoint from which the different objects are viewed.

11. An image processing method executed by at least one hardware processor, the method comprising:

surface data obtaining that includes obtaining, from volume data constituted by a plurality of points, each point having a value, surface data representing a shape of a surface, the shape of the surface being defined by a magnitude of each of the values;

threshold setting that includes setting a threshold for the values, the threshold being used to determine whether to display the surface data;

intersecting-point determining that includes determining an intersecting point at which a straight line passing through a position set as a viewpoint and a point specified by a user intersects with the shape of the surface which is to be displayed in accordance with the threshold; and display controlling that includes controlling, based on a plane passing through the intersecting point, displaying of the shape of the surface represented by the surface data, wherein, in the intersecting-point determining, in response to the surface data representing the shape of the surface being updated as a result of the threshold being changed, the intersecting point at which the straight line passing through the position set as the viewpoint and the point specified by the user intersects with the updated shape of the surface is determined, and wherein, in the display control, based on a plane passing through the intersecting point on the updated shape of the surface, the displaying of the shape of the surface represented by the surface data is controlled.

12. A non-transitory storage medium encoded with a computer-readable program causing a computer to implement:

surface data obtaining processing that includes obtaining, from volume data constituted by a plurality of points, each point having a value, surface data representing a shape of a surface, the shape of the surface being defined by a magnitude of each of the values;

threshold setting processing that includes setting a threshold for the values, the threshold being used to determine whether to display the surface data;

intersecting-point determining processing that includes determining an intersecting point at which a straight line passing through a position set as a viewpoint and a point specified by a user intersects with the shape of the surface which is to be displayed in accordance with the threshold; and display control processing that includes controlling, based on a plane passing through the intersecting point, displaying of the shape of the surface represented by the surface data, wherein, when the surface data representing the shape of the surface is updated as a result of the threshold being changed, the intersecting-point determining processing determines the intersecting point at which the straight line passing through the position set as the viewpoint and the point specified by the user intersects with the updated shape of the surface, and wherein, based on a plane passing through the intersecting point on the updated shape of the surface, the display control processing controls the displaying of the shape of the surface represented by the surface data.

* * * * *